US007781175B2

(12) United States Patent
Fujii et al.

(10) Patent No.: US 7,781,175 B2
(45) Date of Patent: Aug. 24, 2010

(54) METHOD OF SCREENING COMPOUNDS WHICH ALTER THE BINDING PROPERTIES OF GPR39, AND HOMOLOGS THEREOF, TO BILE ACID

(75) Inventors: Ryo Fujii, Osaka (JP); Kazunori Nishi, Ibaraki (JP); Yasuhiro Tanaka, Ibaraki (JP); Masaaki Mori, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 556 days.

(21) Appl. No.: 11/587,285

(22) PCT Filed: Apr. 22, 2005

(86) PCT No.: PCT/JP2005/008271

§ 371 (c)(1),
(2), (4) Date: Oct. 19, 2006

(87) PCT Pub. No.: WO2005/103283

PCT Pub. Date: Nov. 3, 2005

(65) Prior Publication Data

US 2007/0117160 A1      May 24, 2007

(30) Foreign Application Priority Data

Apr. 23, 2004   (JP) .............................. 2004-128169

(51) Int. Cl.
*G01N 33/53*    (2006.01)
*G01N 33/567*   (2006.01)

(52) U.S. Cl. ..................... 435/7.1; 435/7.2; 435/7.21; 435/975

(58) Field of Classification Search ....................... None
See application file for complete search history.

(56) References Cited

U.S. PATENT DOCUMENTS

| 6,599,718 B1* | 7/2003 | Liu et al. .................... 435/69.1 |
| 2002/0004491 A1 | 1/2002 | Xu et al. |
| 2003/0113798 A1* | 6/2003 | Burmer et al. ................ 435/7.1 |
| 2004/0071708 A1 | 4/2004 | Claassen et al. |
| 2004/0171067 A1 | 9/2004 | Hinuma et al. |

FOREIGN PATENT DOCUMENTS

| EP | 1 477 806 A1 | 11/2004 |
| WO | WO-01/81634 A2 | 11/2001 |
| WO | WO-02/39885 A2 | 5/2002 |
| WO | WO-02/061087 A2 | 8/2002 |
| WO | WO-02/071928 A2 | 9/2002 |
| WO | WO-02/079492 A2 | 10/2002 |
| WO | WO-02/086443 A2 | 10/2002 |
| WO | WO-03/071272 A1 | 8/2003 |
| WO | WO-2004/097411 A1 | 11/2004 |

OTHER PUBLICATIONS

Rudling M, et al. Growth Hormone and IDF Research, 9:1-7, 1999.*
Stratagene Catalog, p. 39, 1988.*
Maruyama T, et al. BBRC 298:714-719, 2002.*
Makita N, et al. PNAS 104(13):5443-5448, Mar. 23, 2007.*
Karen Kulju McKee et al., "Cloning and Characterization of Two Human G Protein-Coupled Receptor Genes (GPR38 and GPR39) Related to the Growth Hormone Secretagogue and Neurotensin Receptors"; Genomics, (1997), vol. 46, p. 426-434.
Yuji Kawamata et al., "A G Protein-coupled Receptor Responsive to Bile Acids"; The Journal of Biological Chemistry, (2003), vol. 278, No. 11, Issue of Mar. 14, p. 9435-9440.
Jean-Pierre Raufman et al., "Selective interaction of bile acids with muscarinic receptors: a case of molecular mimicry"; European Journal of Pharmacology (2002), vol. 457, p. 77-84.
Roy G. Smith et al., "Growth Hormone Releasing Substances: Types and Their Receptors"; Hormone Research, (1999); vol. 51 (suppl 3), p. 1-8.
International Search Report with English Translation Thereof and Written Opinion for PCT Application PCT/JP2005/008271.

* cited by examiner

*Primary Examiner*—Robert Landsman
(74) *Attorney, Agent, or Firm*—Edwards Angell Palmer & Dodge LLP; David G. Conlin; Mark D. Russett

(57) ABSTRACT

The present invention relates to screening of an agonist/antagonist, etc. Specifically, the present invention provides a method of screening an agonist or antagonist of a G protein-coupled receptor protein comprising the same or substantially the same amino acid sequence as the amino acid sequence represented by SEQ ID NO: 1, or a salt thereof, which comprises using the receptor protein or a salt thereof and a cholesterol metabolism-related substance, and so on.

5 Claims, 2 Drawing Sheets

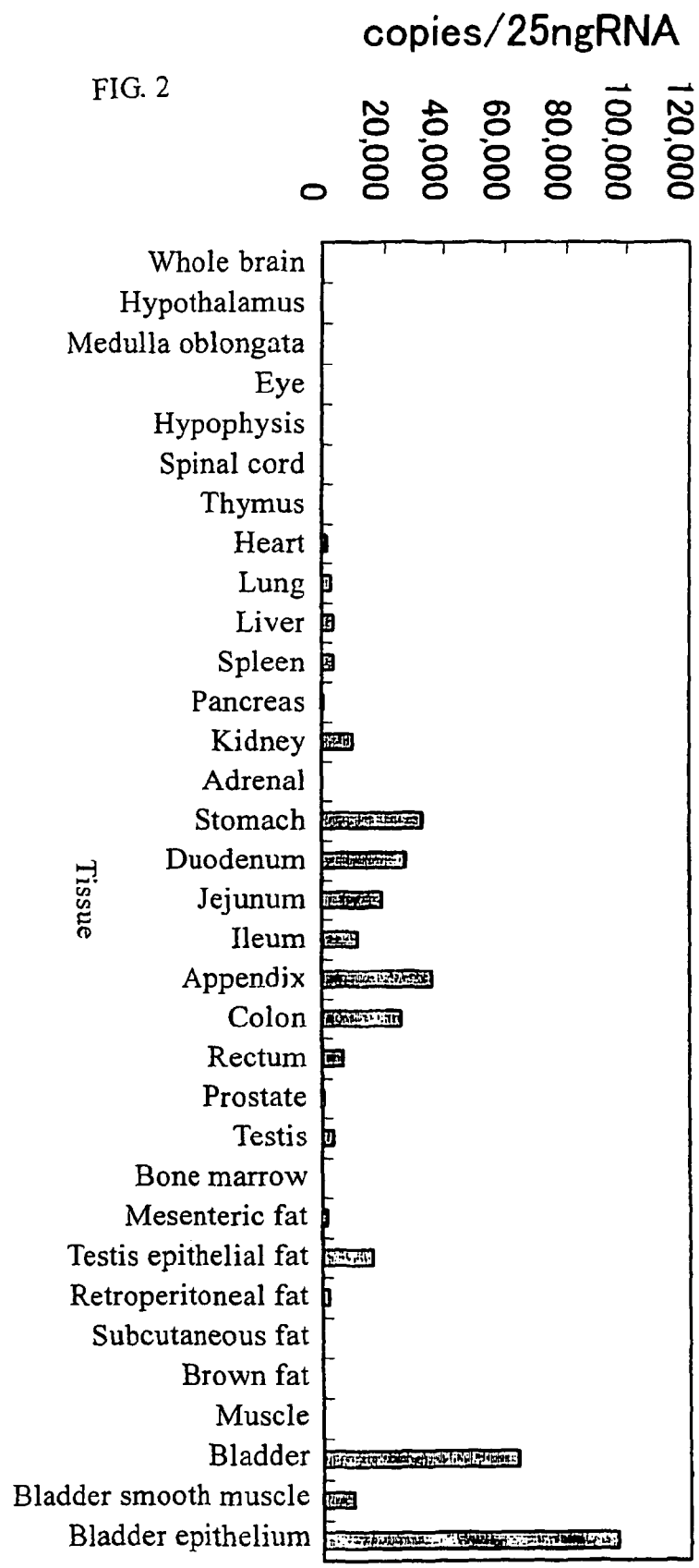

SEQUENCE LISTING

```
<160> NUMBER OF SEQ ID NOS: 9

<210> SEQ ID NO 1
<211> LENGTH: 453
<212> TYPE: PRT
<213> ORGANISM: Homo sapiens

<400> SEQUENCE: 1

Met Ala Ser Pro Ser Leu Pro Gly Ser Asp Cys Ser Gln Ile Ile Asp
                5                   10                  15

His Ser His Val Pro Glu Phe Glu Val Ala Thr Trp Ile Lys Ile Thr
            20                  25                  30

Leu Ile Leu Val Tyr Leu Ile Ile Phe Val Met Gly Leu Leu Gly Asn
        35                  40                  45

Ser Ala Thr Ile Arg Val Thr Gln Val Leu Gln Lys Lys Gly Tyr Leu
    50                  55                  60

Gln Lys Glu Val Thr Asp His Met Val Ser Leu Ala Cys Ser Asp Ile
65                  70                  75                  80

Leu Val Phe Leu Ile Gly Met Pro Met Glu Phe Tyr Ser Ile Ile Trp
                85                  90                  95

Asn Pro Leu Thr Thr Ser Ser Tyr Thr Leu Ser Cys Lys Leu His Thr
            100                 105                 110

Phe Leu Phe Glu Ala Cys Ser Tyr Ala Thr Leu Leu His Val Leu Thr
        115                 120                 125

Leu Ser Phe Glu Arg Tyr Ile Ala Ile Cys His Pro Phe Arg Tyr Lys
    130                 135                 140

Ala Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Thr
                165                 170                 175

Glu Tyr Pro Leu Val Asn Val Pro Ser His Arg Gly Leu Thr Cys Asn
            180                 185                 190

Arg Ser Ser Thr Arg His His Glu Gln Pro Glu Thr Ser Asn Met Ser
        195                 200                 205

Ile Cys Thr Asn Leu Ser Ser Arg Trp Thr Val Phe Gln Ser Ser Ile
    210                 215                 220

Phe Gly Ala Phe Val Val Tyr Leu Val Val Leu Leu Ser Val Ala Phe
225                 230                 235                 240

Met Cys Trp Asn Met Met Gln Val Leu Met Lys Ser Gln Lys Gly Ser
                245                 250                 255

Leu Ala Gly Gly Thr Arg Pro Pro Gln Leu Arg Lys Ser Glu Ser Glu
            260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300
```

```
Met Ala Ala Ala Lys Pro Lys His Asp Trp Thr Arg Ser Tyr Phe Arg
305                 310                 315                 320

Ala Tyr Met Ile Leu Leu Pro Phe Ser Glu Thr Phe Phe Tyr Leu Ser
            325                 330                 335

Ser Val Ile Asn Pro Leu Leu Tyr Thr Val Ser Ser Gln Gln Phe Arg
                340                 345                 350

Arg Val Phe Val Gln Val Leu Cys Cys Arg Leu Ser Leu Gln His Ala
            355                 360                 365

Asn His Glu Lys Arg Leu Arg Val His Ala His Ser Thr Thr Asp Ser
        370                 375                 380

Ala Arg Phe Val Gln Arg Pro Leu Leu Phe Ala Ser Arg Arg Gln Ser
385                 390                 395                 400

Ser Ala Arg Arg Thr Glu Lys Ile Phe Leu Ser Thr Phe Gln Ser Glu
                405                 410                 415

Ala Glu Pro Gln Ser Lys Ser Gln Ser Leu Ser Leu Glu Ser Leu Glu
            420                 425                 430

Pro Asn Ser Gly Ala Lys Pro Ala Asn Ser Ala Ala Glu Asn Gly Phe
        435                 440                 445

Gln Glu His Glu Val
    450

<210> SEQ ID NO 2
<211> LENGTH: 1359
<212> TYPE: DNA
<213> ORGANISM: Homo sapiens

<400> SEQUENCE: 2
atggcttcac ccagcctccc gggcagtgac tgctcccaaa tcattgatca cagtcatgtc      60
cccgagtttg aggtggccac ctggatcaaa atcacccttg ttctggtgta cctgatcatc     120
ttcgtgatgg gccttctggg aacagcgcc accattcggg tcacccaggt gctgcagaag      180
aaaggatact tgcagaagga ggtgacagac acatggtga gtttggcttg ctcggacatc      240
ttggtgttcc tcatcggcat gcccatggag ttctacagca tcatctggaa tcccctgacc      300
acgtccagct acaccctgtc ctgcaagctg cacactttcc tcttcgaggc ctgcagctac      360
gctacgctgc tgcacgtgct gacactcagc tttgagcgct acatcgccat ctgtcacccc      420
ttcaggtaca aggctgtgtc gggaccttgc aggtgaagc tgctgattgg cttcgtctgg      480
gtcacctccg ccctggtggc actgcccttg ctgtttgcca tgggtactga gtacccctg      540 gtgaacgtgc ccagccaccg gggtctcact tgcaaccgct ccagcacccg ccaccacgag      600
cagcccgaga cctccaatat gtccatctgt accaacctct ccagccgctg accgtgttc      660 cagtccagca tcttcggcgc cttcgtggtc tacctcgtgg tcctgctctc cgtagccttc      720
atgtgctgga acatgatgca ggtgctcatg aaaagccaga agggctcgct ggccggggc      780 acgcggcctc cgcagctgag gaagtccgag agcgaagaga gcaggaccgc caggaggcag      840
accatcatct tcctgaggct gattgttgtg acattggccg tatgctggat gcccaaccag      900
attcggagga tcatggctgc ggccaaaccc aagcacgact ggacgaggtc ctacttccgg      960
gcgtacatga tcctcctccc cttctcggag acgtttttct acctcagctc ggtcatcaac     1020
ccgctcctgt acacggtgtc ctcgcagcag tttcggcggg tgttcgtgca ggtgctgtgc     1080
tgccgcctgt cgctgcagca cgccaaccac gagaagcgcc tgcgcgtaca tgcgcactcc     1140
accaccgaca gcgcccgctt tgtgcagcgc ccgttgctct cgcgtcccg gcgccagtcc     1200
```

```
tctgcaagga gaactgagaa gattttctta agcactttc agagcgaggc cgagccccag    1260
tctaagtccc agtcattgag tctcgagtca ctagagccca actcaggcgc gaaaccagcc    1320
aattctgctg cagagaatgg ttttcaggag catgaagtt                          1359
```

<210> SEQ ID NO 3
<211> LENGTH: 456
<212> TYPE: PRT
<213> ORGANISM: Mus musculus

<400> SEQUENCE: 3

```
Met Ala Ser Ser Gly Ser Asn His Ile Cys Ser Arg Val Ile Asp
                 5                  10                  15

His Ser His Val Pro Glu Phe Glu Val Ala Thr Trp Ile Lys Ile Thr
                 20                  25                  30

Leu Ile Leu Val Tyr Leu Ile Phe Val Val Gly Ile Leu Gly Asn
             35                  40                  45

Ser Val Thr Ile Arg Val Thr Gln Val Leu Gln Lys Lys Gly Tyr Leu
     50                  55                  60

Gln Lys Glu Val Thr Asp His Met Val Ser Leu Ala Cys Ser Asp Ile
65                  70                  75                  80

Leu Val Phe Leu Ile Gly Met Pro Met Glu Phe Tyr Ser Ile Ile Trp
                 85                  90                  95

Asn Pro Leu Thr Thr Pro Ser Tyr Ala Leu Ser Cys Lys Leu His Thr
            100                 105                 110

Phe Leu Phe Glu Thr Cys Ser Tyr Ala Thr Leu Leu His Val Leu Thr
        115                 120                 125

Leu Ser Phe Glu Arg Tyr Ile Ala Ile Cys His Pro Phe Lys Tyr Lys
    130                 135                 140

Ala Val Ser Gly Pro Arg Gln Val Lys Leu Leu Ile Gly Phe Val Trp
145                 150                 155                 160

Val Thr Ser Ala Leu Val Ala Leu Pro Leu Leu Phe Ala Met Gly Ile
                165                 170                 175

Glu Tyr Pro Leu Val Asn Val Pro Thr His Lys Gly Leu Asn Cys Asn
            180                 185                 190

Leu Ser Arg Thr Arg His His Asp Glu Pro Gly Asn Ser Asn Met Ser
        195                 200                 205

Ile Cys Thr Asn Leu Ser Asn Arg Trp Glu Val Phe Gln Ser Ser Ile
    210                 215                 220

Phe Gly Ala Phe Ala Val Tyr Leu Val Val Leu Ala Ser Val Ala Phe
225                 230                 235                 240

Met Cys Trp Asn Met Met Lys Val Leu Met Lys Ser Lys Gln Gly Thr
                245                 250                 255

Leu Ala Gly Thr Gly Pro Gln Leu Gln Leu Arg Lys Ser Glu Ser Glu
            260                 265                 270

Glu Ser Arg Thr Ala Arg Arg Gln Thr Ile Ile Phe Leu Arg Leu Ile
        275                 280                 285

Val Val Thr Leu Ala Val Cys Trp Met Pro Asn Gln Ile Arg Arg Ile
    290                 295                 300

Met Ala Ala Ala Lys Pro Lys His Asp Trp Thr Arg Thr Tyr Phe Arg
305                 310                 315                 320

Ala Tyr Met Ile Leu Leu Pro Phe Ser Asp Thr Phe Phe Tyr Leu Ser
                325                 330                 335

Ser Val Val Asn Pro Leu Leu Tyr Asn Val Ser Ser Gln Gln Phe Arg
            340                 345                 350
```

Lys Val Phe Trp Gln Val Leu Cys Cys Arg Leu Thr Leu Gln His Ala
            355                 360                 365

Asn Gln Glu Lys Arg Gln Arg Ala Arg Phe Ile Ser Thr Lys Asp Ser
        370                 375                 380

Thr Ser Ser Ala Arg Ser Pro Leu Ile Phe Leu Ala Ser Arg Arg Ser
385                 390                 395                 400

Asn Ser Ser Arg Arg Thr Asn Lys Val Phe Leu Ser Thr Phe Gln
                405                 410                 415

Thr Glu Ala Lys Pro Gly Glu Ala Lys Pro Gln Pro Leu Ser Pro Glu
            420                 425                 430

Ser Pro Gln Thr Gly Ser Glu Thr Lys Pro Ala Gly Ser Thr Pro Glu
        435                 440                 445

Asn Ser Leu Gln Glu Gln Glu Val
        450                 455

<210> SEQ ID NO 4
<211> LENGTH: 1368
<212> TYPE: DNA
<213> ORGANISM: Mus musculus

<400> SEQUENCE: 4
atggcttcat ccagtggctc caaccacatc tgctcccgtg tcatcgatca tagccatgtt      60
cctgaatttg aggtggccac ttggatcaaa atcaccctca tcttggtgta cctgatcatt     120
tttgtggtag gcatcttggg caacagcgtc accatcaggg ttacgcaggt attgcagaag     180
aagggctatt tgcagaagga ggtgacagat cacatggtca gtttggcttg ttcagatatc     240
ttggtctttt tgattggcat gcccatggag ttctacagca tcatttggaa ccccctgacc     300
acacccagct atgctctgtc ctgtaagctc cacacgttcc tctttgagac gtgcagctac     360
gccacactgc tgcacgtgct gacccctcagc tttgagcgct acattgccat tgtcatcccc     420
ttcaagtata aagcagtgtc tggacctcgc caggtgaaac tgctgattgg ctttgtatgg     480
gtcacctccg ccctggtggc actgcctttg ctctttgcca tgggtatcga gtaccctctg     540
gtaaacgtac ccactcacaa gggactcaac tgcaacctct ctcgcacccg ccaccacgat     600
gaacctggaa actccaatat gtccatctgc acgaacctct ccaaccgttg ggaggtcttc     660
cagtccagca tctttggggc cttgctgtt tacctggtgg tcctggcgtc tgtggctttc     720
atgtgttgga atatgatgaa agtgctaatg aagagcaagc agggcactct tgcagggacc     780
gggccacagc tccagctgag gaagtcagag agtgaggaga gccggacagc aagaagacag     840
accatcatat tcctgagact gattgtggtg acgttggccg tgtgttggat gcccaatcag     900
atccgacgga tcatggctgc agcaaaaccc aaacatgact ggaccagaac gtacttcagg     960
gcatacatga tcctcctgcc cttctctgat accttcttct acctcagctc tgtggtcaac    1020
cctctcctct acaacgtgtc ctctcagcag ttccggaagg tgttctggca ggtgctctgc    1080
tgccgcctga ctctgcagca tgccaaccaa gagaaacgcc agcgtgcccg cttcatctcc    1140
accaaggaca gcaccagctc agcccgcagc cccctcatct tcctagcctc ccggcgcagt    1200
aactcttcct ccaggagaac taacaaggtt ttcttaagca cttttcagac tgaggccaag    1260
cctggagagg ctaagcccca gcccttgagt cctgagtcac cacagactgg ctcagagacc    1320
aaaccagctg gtccaccccc agaaaatagt ttacaggagc aggaagta                  1368

<210> SEQ ID NO 5
<211> LENGTH: 456

```
<212> TYPE: PRT
<213> ORGANISM: Rattus norvegicus

<400> SEQUENCE: 5

Met Ala Ser Ser Gly Ser Ser Asn Ile Cys Ser Arg Val Ile Asp
              5                   10                  15

His Ser His Val Pro Glu Phe Glu Val Ala Thr Trp Ile Lys Ile Thr
             20                  25                  30

Leu Thr Leu Val Tyr Leu Ile Val Phe Val Gly Ile Leu Gly Asn
             35                  40                  45

Ser Val Thr Ile Arg Val Thr Gln Val Leu Gln Lys Lys Gly Tyr Leu
50                   55                  60

Gln Lys Glu Val Thr Asp His Met Ile Ser Leu Ala Cys Ser Asp Ile
65                   70                  75                  80

Leu Val Phe Leu Ile Gly Met Pro Met Glu Phe Tyr Ser Ile Ile Trp
                 85                  90                  95

Asn Pro Leu Thr Thr Pro Ser Tyr Ala Leu Ser Cys Lys Leu His Thr
             100                 105                 110

Phe Leu Phe Glu Thr Cys Ser Tyr Ala Thr Leu Leu His Val Leu Thr
             115                 120                 125

Leu Ser Phe Glu Arg Tyr Ile Ala Ile Cys His Pro Phe Arg Tyr Lys
130                 135                 140

Asp Val Ser Gly Pro Cys Gln Val Lys Leu Leu Ile Gly Phe Val Trp
145                 150                 155                 160

Val Thr Ser Ala Leu Val Ala Leu Pro Leu Leu Phe Ala Met Gly Ile
                 165                 170                 175

Glu Tyr Pro Leu Ala Asn Val Pro Thr His Lys Gly Leu Asn Cys Asn
             180                 185                 190

Leu Ser Arg Thr Arg His His Asp His Pro Gly Asp Ser Asn Met Ser
             195                 200                 205

Ile Cys Thr Asn Leu Ser Ser Arg Trp Glu Val Phe Gln Ser Ser Ile
210                 215                 220

Phe Gly Ala Phe Ala Val Tyr Leu Val Val Leu Val Ser Val Ala Phe
225                 230                 235                 240

Met Cys Trp Asn Met Met Lys Val Leu Met Lys Ser Lys Arg Gly Thr
                 245                 250                 255

Leu Ala Gly Thr Gly Pro Gln Leu Gln Leu Arg Lys Ser Glu Ser Glu
             260                 265                 270

Glu Ser Arg Thr Ala Arg Arg Gln Thr Ile Ile Phe Leu Arg Leu Ile
             275                 280                 285

Val Val Thr Leu Ala Val Cys Trp Met Pro Asn Gln Ile Arg Arg Ile
290                 295                 300

Met Ala Ala Ala Lys Pro Lys His Asp Trp Thr Lys Ser Tyr Phe Lys
305                 310                 315                 320

Ala Tyr Met Ile Leu Leu Pro Phe Ser Asp Thr Phe Phe Tyr Leu Ser
                 325                 330                 335

Ser Val Val Asn Pro Leu Leu Tyr Asn Val Ser Ser Gln Gln Phe Arg
             340                 345                 350

Lys Val Phe Trp Gln Val Leu Cys Cys Arg Leu Thr Leu Gln His Ala
             355                 360                 365

Asn Gln Glu Lys Gln Gln Arg Ala Tyr Phe Ser Ser Thr Lys Asn Ser
370                 375                 380

Ser Arg Ser Ala Arg Ser Pro Leu Ile Phe Leu Ala Ser Arg Arg Ser
385                 390                 395                 400
```

-continued

```
Asn Ser Ser Ser Arg Arg Thr Asn Lys Val Phe Leu Ser Thr Phe Gln
            405                 410                 415

Ala Glu Ala Lys Pro Leu Glu Gly Glu His Gln Pro Leu Ser Pro Glu
        420                 425                 430

Ser Pro Gln Thr Gly Ser Glu Thr Lys Pro Ala Gly Ser Ala Thr Glu
    435                 440                 445

Asn Ser Leu Gln Glu Gln Glu Val
    450                 455
```

<210> SEQ ID NO 6
<211> LENGTH: 1367
<212> TYPE: DNA
<213> ORGANISM: Rattus norvegicus

<400> SEQUENCE: 6

| | | | | | |
|---|---|---|---|---|---|
| atggcttcat | ccagtggctc | cagcaacatc | tgctcccgag | tcatcgatca | cagccatgtc | 60 |
| cctgagttcg | aagtggccac | ttggatcaaa | atcaccctca | ccttggtgta | cctgatcgtc | 120 |
| ttcgtggtag | gcatcttggg | caatagcgtc | accatccggg | ttacgcaggt | attgcagaaa | 180 |
| aagggctatt | tgcagaagga | ggtgacagat | cacatgatca | gtttggcttg | ttcagatatc | 240 |
| ttggtcttt | tgattggcat | gcccatggag | ttctacagca | tcatctggaa | cccccctgacc | 300 |
| acacccagct | atgctctgtc | ctgcaagctc | cacacgttcc | tctttgagac | gtgtagctac | 360 |
| gccacattgc | tgcatgtgct | gacccctcagc | tttgagcgct | acattgccat | ttgtcatccc | 420 |
| ttcagatata | aggacgtgtc | tggaccttgc | caggtgaaac | tgctgatcgg | ctttgtatgg | 480 |
| gtcacctccg | ctctggtggc | actgcccttg | ctctttgcca | tgggtattga | gtaccctctg | 540 |
| gcgaacgtcc | ccactcacaa | gggactcaac | tgtaacctct | ctcgtacccg | ccaccacgat | 600 |
| catcctggag | actccaatat | gtccatctgc | acgaacctct | ccagccgttg | ggaggtcttc | 660 |
| cagtccagca | tctttgggc | cttcgctgtt | tacctggtgg | tcctggtgtc | tgtggctttc | 720 |
| atgtgttgga | acatgatgaa | agtgctaatg | aagagcaagc | ggggtactct | ggcagggacc | 780 |
| ggaccacagc | tgcagctgcg | gaagtcagag | agtgaggaga | gccggacagc | gagaagacag | 840 |
| accatcatat | tcctgagact | gatcgtggtg | acactggccg | tgtgttggat | gccaaatcag | 900 |
| atccgacgga | tcatggccgc | agcaaaaccc | aaacatgact | ggaccaagtc | gtacttcaag | 960 |
| gcgtacatga | tcctcctccc | cttctccgac | accttcttct | acctcagctc | cgtggtcaac | 1020 |
| cctctcctct | acaacgtgtc | ttctcagcag | ttccggaagg | ttttctggca | ggttctctgc | 1080 |
| tgccggctga | ctctgcagca | tgccaaccag | gagaaacagc | agcgtgccta | cttcagctct | 1140 |
| accaaaaaca | gcagccgctc | agcccgaagc | ccgctcatct | tcctagcctc | ccggcgtagt | 1200 |
| aactcttcct | cccggagaac | taacaaggtt | ttcttaagca | cttttcaggc | ggaggctaag | 1260 |
| cctctagagg | gcgagcacca | gcccttgagt | cctgagtcac | cacagaccgg | ctcagagacc | 1320 |
| aaacctgctg | gttccgccac | agaaaatagt | ttacaggagc | aggaagt | | 1367 |

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cccatggagt tctacagcat cat                                             23

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tgtggagctt gcaggacaga                                                    20

<210> SEQ ID NO 9
<211> LENGTH: 22
<212> TYPE: DNA
<213> ORGANISM: Artificial Sequence
<220> FEATURE:
<223> OTHER INFORMATION: Probe

<400> SEQUENCE: 9
tggaaccccc tgaccacacc ca                                                 22
```

METHOD OF SCREENING COMPOUNDS WHICH ALTER THE BINDING PROPERTIES OF GPR39, AND HOMOLOGS THEREOF, TO BILE ACID

CROSS-REFERENCE TO RELATED APPLICATIONS

This application is the 35 U.S.C. §371 national stage of PCT application PCT/JP2005/008271, filed Apr. 22, 2005, which claims priority to Japanese patent application no. 128169/2004, filed Apr. 23, 2004. The contents of these applications are incorporated herein by reference in their entirety.

TECHNICAL FIELD

The present invention relates to use of a G protein-coupled receptor protein (GPR39).

BACKGROUND ART

Physiologically active substances such as various hormones, neurotransmitters and the like regulate the biological functions through specific receptor proteins present on cell membranes. Many of these receptor proteins are coupled with guanine nucleotide-binding protein (hereinafter sometimes simply referred to as G protein) and mediate the intracellular signal transduction through activation of G protein. These receptor proteins have the common structure having seven transmembrane domains and are thus collectively referred to as G protein-coupled receptor proteins or seven-transmembrane receptor proteins (7TMR).

G protein-coupled receptor proteins are present on the cell surface of each functional cell and organ in an organism, and play critical physiological roles as the target of the molecules that regulate the functions of the cell and organ, e.g., physiologically active substances such as peptide hormones, nucleic acids, amines, phospholipids, etc. Receptors transmit signals to cells through binding with physiologically active substances, and the signals induce various reactions such as activation or suppression of the cells.

To clarify the relationship between substances that regulate complex functions within cells and organs in various organisms, and their specific receptor proteins, in particular, G protein-coupled receptor proteins, would elucidate the functions of cells and organs in various organisms to provide a very important means for development of medicaments closely associated with these functions.

For example, in various organs, their physiological functions are controlled in vivo through regulation by many hormones, hormone-like substances, neurotransmitters or physiologically active substances. In particular, physiologically active substances are found in numerous sites of the body and regulate the physiological functions through their corresponding receptor proteins. Many unknown hormones, neurotransmitters or many other physiologically active substances are assumed to exist more in the body and, as to their receptor proteins, many of these proteins have not yet been reported. In addition, it is yet unknown if there are subtypes of known receptor proteins or differences between animal species.

It is a very important means for development of medicaments to clarify the relationship between substances that regulate elaborate functions in vivo and their specific receptor proteins. Further in development of drugs, it is required for efficient screening of agonists and antagonists of receptor proteins to clarify functional mechanisms of genes for the receptor protein expressed in vivo and express the genes in an appropriate expression system.

In recent years, random analysis of cDNA sequences has been actively studied as a means for analyzing genes expressed in vivo. The sequences of cDNA fragments thus obtained have been registered on and published to databases as Expressed Sequence Tag (EST). In addition, it has been extensively attempted to predict unknown genes based on the analysis of genomic sequences. However, since many ESTs or genomic sequences contain sequence information only, it is difficult to estimate their functions from that information.

The amino acid sequences of human-derived GPR39 and DNAs encoding the same are reported (Genomics 1997 Dec. 15, 46 (3): 426-34; WO 2002/61087; US 2002/004491; WO 2002/39885; WO 2002/71928; WO 2001/81634; WO 2002/79492; WO 2002/86443). However, the functions of these G protein-coupled receptor proteins and their physiological ligands remain unsolved.

DISCLOSURE OF INVENTION

Heretofore, substances that inhibit the binding of G protein-coupled receptor proteins to physiologically active substances (i.e., ligands) and substances that bind and induce signals as in physiologically active substances (i.e., ligands) have been utilized for medicaments as antagonists or agonists specific to these receptor proteins that regulate the biological functions. Therefore, it is a very important means in search for agonists or antagonists that can be targeted for development of medicaments to determine specific ligands for G protein-coupled receptor proteins.

However, many G protein-coupled receptor proteins with unknown functions and many so-called orphan receptor proteins in which the corresponding ligands are yet unidentified are present even at this point of time. Thus, search of ligands for G protein-coupled receptor proteins and elucidation of their functions are eagerly awaited.

G protein-coupled receptor proteins are useful in search for novel physiological active substances (i.e., ligands) using the signal transduction activity as an indicator and in search for agonists and antagonists of the receptor proteins. On the other hand, even if any physiological ligand is not found, it is possible to prepare agonists and antagonist of the receptor protein by analyzing physiological actions of the receptor proteins through inactivation experiments of the receptor proteins (knockout animal). Ligands, agonists or antagonists, etc. of these receptor proteins are expected to be utilized as preventive/therapeutic agents and diagnostic agents for diseases associated with dysfunction or hyperfunction of the G protein-coupled receptor proteins.

Moreover, attenuation or accentuation in the functions of G protein-coupled receptor proteins due to genetic aberration of the G protein-coupled receptor proteins in the body causes some disorders in many cases. In this case, the G protein coupled receptor proteins can be applied not only to administration of antagonists or agonists of the receptor proteins, but also to gene therapy by transfer of the receptor protein gene into the body (or some particular organs) or by introduction of the antisense nucleic acid of the receptor protein gene. In this case, information on the base sequence of the receptor protein is essentially required for investigating deletion or mutation on the gene. The genes for the receptor proteins are also applicable as preventive/therapeutic agents and diagnostic agents for diseases associated with dysfunction of the receptor protein.

The present invention relates to determination of a ligand for orphan G protein-coupled receptor protein GPR39, whose function is unknown, and to use of the G protein-coupled receptor protein and its ligand. More particularly, the present invention provides a method of screening a compound (antagonist or agonist) or its salt that alters the binding properties of the ligand to the G protein-coupled receptor protein, a kit for the screening, a compound (antagonist or agonist) or its salt that alters the binding properties of the ligand to the G protein-coupled receptor protein, which is obtainable using the screening method or the screening kit, and a medicament comprising a compound (antagonist or agonist) or its salt that alters the binding properties of the ligand to the G protein-coupled receptor protein or a compound or its salt that alters the expression level of the G protein-coupled receptor protein, etc.

The present inventors have made extensive investigations and as a result, found that a ligand for human-derived GPR39 is a cholesterol metabolism-related substance. Based on these findings, the inventors have continued further investigations and come to accomplish the present invention.

That is, the present invention provides the following embodiments, and so on.

[1] A method of screening (I) a compound or its salt that alters the binding property of a G protein-coupled receptor protein comprising the same or substantially the same amino acid sequence as the amino acid sequence represented by SEQ ID NO: 1, or a salt thereof, to a cholesterol metabolism-related substance, or (II) a compound or its salt that modulates the signal transduction induced by the binding of said receptor protein or a salt thereof to a cholesterol metabolism-related substance, which comprises using (1) said receptor protein, a partial peptide thereof, or a salt thereof and (2) the cholesterol metabolism-related substance.

[2] A method of screening an agonist or antagonist of a G protein-coupled receptor protein comprising the same or substantially the same amino acid sequence as the amino acid sequence represented by SEQ ID NO: 1, or a salt thereof, which comprises using (1) said receptor protein, a partial peptide thereof, or a salt thereof and (2) a compound or its salt that alters the binding property of said receptor protein or a salt thereof to a cholesterol metabolism-related substance.

[3] The screening method according to [1] or [2] described above, wherein the G protein-coupled receptor protein is a G protein-coupled receptor protein consisting of the amino acid sequence represented by SEQ ID NO: 1, SEQ ID NO: 3 or SEQ ID NO: 5.

[4] A kit for screening (I) a compound or its salt that alters the binding property of a G protein-coupled receptor protein comprising the same or substantially the same amino acid sequence as the amino acid sequence represented by SEQ ID NO: 1, or a salt thereof, to a cholesterol metabolism-related substance, or (II) a compound or its salt that modulates the signal transduction induced by binding of said receptor protein or a salt thereof to a cholesterol metabolism-related substance, which comprises (1) said receptor protein, a partial peptide thereof, or a salt thereof and (2) the cholesterol metabolism-related substance.

[5] A kit for screening an agonist or antagonist of a G protein-coupled receptor protein comprising the same or substantially the same amino acid sequence as the amino acid sequence represented by SEQ ID NO: 1, or a salt thereof, which comprises (1) said receptor protein, a partial peptide thereof, or a salt thereof and (2) a compound or its salt that alters the binding property of said receptor protein or a salt thereof to a cholesterol metabolism-related substance.

[6] (I) A compound or its salt that alters the binding property of a G protein-coupled receptor protein comprising the same or substantially the same amino acid sequence as the amino acid sequence represented by SEQ ID NO: 1, or a salt thereof, to a cholesterol metabolism-related substance, or (II) a compound or its salt that modulates the signal transduction induced by binding of said receptor protein or a salt thereof to a cholesterol metabolism-related substance, which is obtainable using the screening method according to [1] described above or the screening kit according to [4] described above.

[7] A medicament comprising (I) a compound or its salt that alters the binding property of a cholesterol metabolism-related substance to a G protein-coupled receptor protein comprising the same or substantially the same amino acid sequence as the amino acid sequence represented by SEQ ID NO: 1, or a salt thereof, or (II) a compound or its salt that modulates the signal transduction induced by binding of a cholesterol metabolism-related substance to a G protein-coupled receptor protein comprising the same or substantially the same amino acid sequence as the amino acid sequence represented by SEQ ID NO: 1, or a salt thereof.

[8] An agonist or antagonist of the G protein-coupled receptor protein comprising the same or substantially the same amino acid sequence as the amino acid sequence represented by SEQ ID NO: 1, or a salt thereof, which is obtainable using the screening method according to [2] described above or the screening kit according to [5] described above.

[9] A medicament comprising an agonist or antagonist of a G protein-coupled receptor protein comprising the same or substantially the same amino acid sequence as the amino acid sequence represented by SEQ ID NO: 1, or a salt thereof.

[10] A preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises an antagonist of a G protein-coupled receptor protein comprising the same or substantially the same amino acid sequence as the amino acid sequence represented by SEQ ID NO: 1, or a salt thereof.

[11] An antiemetic agent, which comprises an antagonist of a G protein-coupled receptor protein comprising the same or substantially the same amino acid sequence as the amino acid sequence represented by SEQ ID NO: 1, or a salt thereof, for vomiting which may be induced by functional bowel disorders caused by gastrointestinal motility disturbances, irritable bowel syndrome, fecal incontinence, colitis or Crohn's disease.

[12] A diagnostic agent, which comprises a polynucleotide comprising a polynucleotide encoding a G protein-coupled receptor protein comprising the same or substantially the same amino acid sequence as the amino acid sequence represented by SEQ ID NO: 1, or a partial peptide thereof, for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization.

[13] A preventive/therapeutic agent for preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises an antibody to a G protein-coupled receptor protein comprising the same or substantially the same amino acid sequence as the amino acid sequence represented by SEQ ID NO: 1, a partial peptide thereof, or a salt thereof.

[14] An antiemetic agent, which comprises an antibody to a G protein-coupled receptor protein comprising the same or substantially the same amino acid sequence as the amino acid sequence represented by SEQ ID NO: 1, a partial peptide thereof, or a salt thereof, for vomiting which may be induced by functional bowel disorders caused by gastrointestinal motility disturbances, irritable bowel syndrome, fecal incontinence, colitis or Crohn's disease.

[15] A diagnostic agent, which comprises an antibody to a G protein-coupled receptor protein comprising the same or substantially the same amino acid sequence as the amino acid sequence represented by SEQ ID NO: 1, a partial peptide thereof, or a salt thereof, for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization.

[16] A preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof.

[17] An antiemetic agent, which comprises a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, for vomiting which may be induced by functional bowel disorders caused by gastrointestinal motility disturbances, irritable bowel syndrome, fecal incontinence, colitis or Crohn's disease.

[18] A method of screening a compound or its salt that alters the expression level of a G protein-coupled receptor protein comprising the same or substantially the same amino acid sequence as the amino acid sequence represented by SEQ ID NO: 1, to prevent/treat (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises using a polynucleotide comprising a polynucleotide encoding said receptor protein or a partial peptide thereof.

[19] A method of screening a compound or its salt that alters the expression level of a G protein-coupled receptor protein comprising the same or substantially the same amino acid sequence as the amino acid sequence represented by SEQ ID NO: 1, to prevent vomiting which may be induced by functional bowel disorders caused by gastrointestinal motility disturbances, irritable bowel syndrome, fecal incontinence, colitis or Crohn's disease, which comprises using a polynucleotide comprising a polynucleotide encoding said receptor protein or a partial peptide thereof.

[20] A kit for screening a compound or its salt that alters the expression level of a G protein-coupled receptor protein comprising the same or substantially the same amino acid sequence as the amino acid sequence represented by SEQ ID NO: 1, to prevent/treat (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises a polynucleotide comprising a polynucleotide encoding said receptor protein or a partial peptide thereof.

[21] A kit for screening a compound or its salt that alters the expression level of a G protein-coupled receptor protein comprising the same or substantially the same amino acid sequence as the amino acid sequence represented by SEQ ID NO: 1, to prevent vomiting which may be induced by functional bowel disorders caused by gastrointestinal motility disturbances, irritable bowel syndrome, fecal incontinence, colitis or Crohn's disease, which comprises a polynucleotide comprising a polynucleotide encoding said receptor protein or a partial peptide thereof.

[22] A compound or its salt that alters the expression level of a G protein-coupled receptor protein comprising the same or substantially the same amino acid sequence as the amino acid sequence represented by SEQ ID NO: 1, or a partial peptide thereof, to prevent/treat (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which is obtainable using the screening method according to [18] described above or the screening kit according to [20] described above.

[23] A compound or its salt that alters the expression level of a G protein-coupled receptor protein comprising the same or substantially the same amino acid sequence as the amino acid sequence represented by SEQ ID NO: 1, or a partial peptide thereof, to prevent/treat vomiting which may be induced by functional bowel disorders caused by gastrointestinal motility disturbances, irritable bowel syndrome, fecal incontinence, colitis or Crohn's disease, which is obtainable using the screening method according to [19] described above or the screening kit according to [21] described above.

[24] A preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises a compound or its salt that decreases the expression level of a G protein-coupled receptor protein comprising the same or substantially the same amino acid sequence as the amino acid sequence represented by SEQ ID NO: 1, or a partial peptide thereof.

[25] An antiemetic agent for vomiting which may be induced by functional bowel disorders caused by gastrointestinal motility disturbances, irritable bowel syndrome, fecal incontinence, colitis or Crohn's disease, which comprises a compound or its salt that decreases the expression level of a G protein-coupled receptor protein comprising the same or substantially the same amino acid sequence as the amino acid sequence represented by SEQ ID NO: 1, or a partial peptide thereof.

[26] A method of preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, which comprises administering to a mammal an effective dose of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a partial peptide thereof.

[27] A method of preventing vomiting which may be induced by functional bowel disorders caused by gastrointestinal motility disturbances, irritable bowel syndrome, fecal incontinence, colitis or Crohn's disease, which comprises administering to a mammal an effective dose of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a partial peptide thereof.

[28] Use of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a partial peptide thereof, to manufacture a preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization.

[29] Use of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a partial peptide thereof, to manufacture an antiemetic agent for vomiting which may be induced by functional bowel disorders caused by gastrointestinal motility disturbances, irritable bowel syndrome, fecal incontinence, colitis or Crohn's disease.

The present invention further provides the following embodiments, and so on.

[30] The screening method according to [1] described above, which comprises comparing (i) the case where a G protein-coupled receptor protein comprising the same or substantially the same amino acid sequence as the amino acid sequence represented by SEQ ID NO: 1 (hereinafter briefly referred to as GPR39), its partial peptide, or a salt thereof is brought in contact with the cholesterol metabolism-related substance, with (ii) the case where the GPR39, its partial peptide, or a salt thereof, is contacted with the cholesterol metabolism-related substance and a test compound or its salt.

[31] The screening method according to [1] described above, which comprises measuring the binding amounts of a labeled cholesterol metabolism-related substance to the GPR39, its partial peptide, or a salt thereof, (i) when the labeled cholesterol metabolism-related substance is brought in contact with the GPR39, its partial peptide, or a salt thereof, and (ii) when the labeled cholesterol metabolism-related substance and a test compound or its salt are brought in contact with the GPR39, its partial peptide, or a salt thereof; and comparing the binding amounts measured in (i) and (ii).

[32] The screening method according to [1] described above, which comprises measuring the binding amounts of a labeled cholesterol metabolism-related substance to a cell containing the GPR39, (i) when the labeled cholesterol metabolism-related substance is brought in contact with the cell containing the GPR39, and (ii) when the labeled cholesterol metabolism-related substance and a test compound or its salt are brought in contact with the cell containing the GPR39; and comparing the binding amounts measured in (i) and (ii). [33] The screening method according to [1] described above, which comprises measuring the binding amounts of a labeled cholesterol metabolism-related substance to a membrane fraction of cell containing the GPR39, (i) when the labeled cholesterol metabolism-related substance is brought in contact with the membrane fraction of cell containing the GPR39, and (ii) when the labeled cholesterol metabolism-related substance and a test compound or its salt are brought in contact with the membrane fraction of the cell; and comparing the binding amounts measured in (i) and (ii).

[34] The screening method according to [1] described above, which comprises measuring the binding amounts of a labeled cholesterol metabolism-related substance to the GPR39, (i) when the labeled cholesterol metabolism-related substance is brought in contact with the GPR39 expressed in a transformant or its cell membrane (preferably the cell membrane) by culturing the transformant transformed with a recombinant vector bearing DNA comprising DNA encoding the GPR39 and (ii) when the labeled cholesterol metabolism-related substance and a test compound or its salt are brought in contact with the GPR39 expressed in the transformant or its cell membrane (preferably the cell membrane) and comparing the binding amounts measured in (i) and (ii).

[35] The screening method according to [1] described above, which comprises measuring the GPR39-mediated cell stimulating activities, (i) when a compound or its salt that activates the GPR39 is brought in contact with a cell containing the GPR39, and (ii) when a compound or its salt that activates the GPR39 and a test compound are brought in contact with a cell containing the GPR39; and comparing the activities measured in (i) and (ii).

[36] The screening method according to [1] described above, which comprises measuring the GPR39-mediated cell stimulating activities, (i) when a compound or its salt that activates the GPR39 is brought in contact with the GPR39 expressed in a transformant or its cell membrane (preferably the cell membrane) by culturing the transformant transformed with a recombinant vector bearing DNA comprising DNA encoding the GPR39 and (ii) when a compound or its salt that activates the GPR39 and a test compound are brought in contact with the GPR39 expressed in the transformant or its cell membrane (preferably the cell membrane) and comparing the activities measured in (i) and (ii).

[37] The screening method according to [35] or [36] described above, wherein the compound that activates the GPR39 is a cholesterol metabolism-related substance.

[38] The screening kit according to [4] or [5] described above, which comprises a cell containing the GPR39 or its membrane fraction.

[39] The screening kit according to [4] or [5] described above, which comprises the GPR39 expressed in a transformant or its cell membrane (preferably the cell membrane) by culturing the transformant transformed with a recombinant vector bearing DNA comprising DNA encoding the GPR39.

[40] A method for confirmation that a preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, binds to a G protein-coupled receptor protein comprising the same or substantially the same amino acid sequence represented by SEQ ID NO: 1, or a salt thereof, which comprises using the receptor protein or a salt thereof.

[41] A method for confirmation that an antiemetic agent for vomiting which may be induced by functional bowel disorders caused by gastrointestinal motility disturbances, irritable bowel syndrome, fecal incontinence, colitis or Crohn's disease binds to a G protein-coupled receptor protein comprising the same or substantially the same amino acid sequence represented by SEQ ID NO: 1, or a salt thereof, which comprises using the receptor protein or a salt thereof.

[42] A method for confirmation that a preventive/therapeutic agent for (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization is an antagonist of a G protein-coupled receptor protein comprising the same or substantially the same amino acid sequence represented by SEQ ID NO: 1, or a salt thereof, which comprises using the receptor protein or a salt thereof.

[43] A method for confirmation that an antiemetic agent for vomiting which may be induced by functional bowel disorders caused by gastrointestinal motility disturbances, irritable bowel syndrome, fecal incontinence, colitis or Crohn's disease is an antagonist of a G protein-coupled receptor protein comprising the same or substantially the same amino acid sequence represented by SEQ ID NO: 1, or a salt thereof, which comprises using the receptor protein or a salt thereof.

[44] The method for confirmation according to any one of [40] through [43] described above, which comprises measuring the binding amounts of each agent to the receptor protein, its partial peptide, or a salt thereof, when each agent is brought in contact with the receptor protein, its partial peptide, or a salt thereof.

[45] The medicament according to [7] described above, which is a preventive/therapeutic agent for a disease caused by binding of a cholesterol metabolism-related substance to a G protein-coupled receptor protein comprising the same or substantially the same amino acid sequence represented by SEQ ID NO: 1, or a salt thereof.

[46] A preventive/therapeutic agent for a disease caused by binding of a cholesterol metabolism-related substance to a G protein-coupled receptor protein comprising the same or substantially the same amino acid sequence represented by SEQ ID NO: 1, or a salt thereof, which comprises an antagonist of a G protein-coupled receptor protein comprising the same or substantially the same amino acid sequence represented by SEQ ID NO: 1, or a salt thereof.

[47] A diagnostic agent for a disease caused by binding of a cholesterol metabolism-related substance to a G protein-coupled receptor protein comprising the same or substantially the same amino acid sequence represented by SEQ ID NO: 1, or a salt thereof, which comprises a polynucleotide comprising a polynucleotide encoding a G protein-coupled receptor protein comprising the same or substantially the same amino acid sequence represented by SEQ ID NO: 1, or its partial peptide.

[48] A preventive/therapeutic agent for a disease caused by binding of a cholesterol metabolism-related substance to a G protein-coupled receptor protein comprising the same or substantially the same amino acid sequence represented by SEQ ID NO: 1, or a salt thereof, which comprises an antibody to a G protein-coupled receptor protein comprising the same or substantially the same amino acid sequence represented by SEQ ID NO: 1, its partial peptide, or a salt thereof.

[49] A diagnostic agent for a disease caused by binding of a cholesterol metabolism-related substance to a G protein-coupled receptor protein comprising the same or substantially the same amino acid sequence represented by SEQ ID NO: 1, or a salt thereof, which comprises an antibody to a G protein-coupled receptor protein comprising the same or substantially the same amino acid sequence represented by SEQ ID NO: 1, its partial peptide, or a salt thereof.

[50] A preventive/therapeutic agent for a disease caused by binding of a cholesterol metabolism-related substance to a G protein-coupled receptor protein comprising the same or substantially the same amino acid sequence represented by SEQ ID NO: 1, or a salt thereof, which comprises a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof.

[51] A preventive/therapeutic agent for a disease caused by binding of a cholesterol metabolism-related substance to a G protein-coupled receptor protein comprising the same or substantially the same amino acid sequence represented by SEQ ID NO: 1, or a salt thereof, which comprises a compound or its salt that decreases the expression level of a G protein-coupled receptor protein comprising the same or substantially the same amino acid sequence as the amino acid sequence represented by SEQ ID NO: 1, or a salt thereof.

[52] The agent according to any one of [46] through [51] described above, wherein the disease caused by binding of a cholesterol metabolism-related substance to a G protein-coupled receptor protein comprising the same or substantially the same amino acid sequence represented by SEQ ID NO: 1, or a salt thereof, is (i) inflammatory bowel disorder, (ii) functional bowel disorders caused by gastrointestinal motility disturbances, (iii) irritable bowel syndrome, (iv) fecal incontinence, (v) colitis, (vi) posttransplantational hyperimmunization or (vii) vomiting which may be induced by functional bowel disorders caused by gastrointestinal motility disturbances, irritable bowel syndrome, fecal incontinence, colitis or Crohn's disease.

[53] A method of preventing/treating a disease caused by binding of a cholesterol metabolism-related substance to a G protein-coupled receptor protein comprising the same or substantially the same amino acid sequence as the amino acid sequence represented by SEQ ID NO: 1, or a salt thereof, which comprises inhibiting (I) the binding property of a cholesterol metabolism-related substance to a G protein-coupled receptor protein comprising the same or substantially the same amino acid sequence as the amino acid sequence represented by SEQ ID NO: 1, or a salt thereof, or (II) the signal transduction induced by binding of a cholesterol metabolism-related substance to a G protein-coupled receptor protein comprising the same or substantially the same amino acid sequence as the amino acid sequence represented by SEQ ID NO: 1, or a salt thereof.

[54] A method of preventing/treating a disease caused by binding of a cholesterol metabolism-related substance to a G protein-coupled receptor protein comprising the same or substantially the same amino acid sequence as the amino acid sequence represented by SEQ ID NO: 1, or a salt thereof, which comprises decreasing the expression level of a G protein-coupled receptor protein comprising the same or substantially the same amino acid sequence as the amino acid sequence represented by SEQ ID NO: 1, or a salt thereof.

[55] A method of preventing/treating a disease caused by binding of a cholesterol metabolism-related substance to a G protein-coupled receptor protein comprising the same or substantially the same amino acid sequence as the amino acid sequence represented by SEQ ID NO: 1, or a salt thereof, which comprises administering to a mammal an effective dose of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a salt thereof.

[56] Use of (i) an antibody to a G protein-coupled receptor protein comprising the same or substantially the same amino acid sequence as the amino acid sequence represented by SEQ ID NO: 1, a partial peptide thereof, or a salt thereof, (ii) a polynucleotide comprising the entire or part of a base sequence complementary to a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an antagonist of a G protein-coupled receptor protein comprising the same or substantially the same amino acid sequence as the amino acid sequence represented by SEQ ID NO: 1, or a salt thereof, or (iv) a compound or its salt that decreases the expression level of a G protein-coupled receptor protein comprising the same or substantially the same amino acid sequence as the amino acid sequence represented by SEQ ID NO: 1, or a salt thereof, to manufacture a preventive/therapeutic agent for a disease caused by binding of a cholesterol metabolism-related substance to a G protein-coupled receptor protein comprising the same or substantially the same amino acid sequence represented by SEQ ID NO: 1, or a salt thereof.

[57] The medicament according to [7] described above, which is a preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof.

[58] A preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises an agonist to said receptor protein, which agonist potentiates the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof.

[59] A preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises a cholesterol metabolism-related substance.

[60] A diagnostic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises a polynucleotide comprising a polynucleotide encoding a G protein-coupled receptor protein comprising the same or substantially the same amino acid sequence represented by SEQ ID NO: 1, or its partial peptide.

[61] A preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises a polynucleotide comprising a polynucleotide encoding a G protein-coupled receptor protein comprising the same or substantially the same amino acid sequence represented by SEQ ID NO: 1, or its partial peptide.

[62] A preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises a G protein-coupled receptor protein comprising the same or substantially the same amino acid sequence represented by SEQ ID NO: 1, its partial peptide, or a salt thereof.

[63] A diagnostic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises an antibody to a G protein-coupled receptor protein comprising the same or substantially the same amino acid sequence represented by SEQ ID NO: 1, its partial peptide, or a salt thereof.

[64] A preventive/therapeutic agent for (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises a compound or its salt that increases the expression level of a G protein-coupled receptor protein comprising the same or substantially the same amino acid sequence represented by SEQ ID NO: 1, or a salt thereof.

[65] The agent according to any one of [58] through [64] described above, wherein (a) the disease associated with dysfunction of a G protein-coupled receptor protein comprising the same or substantially the same amino acid sequence as the amino acid sequence represented by SEQ ID NO: 1, or a salt thereof; (b) the disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof, or (c) the disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof is growth retardation, lacerations, burn injury, poor circulation, decline in learning ability, hypogonadism, dysgeusia, anosmia, hyperplasia, arteriosclerosis, myocardial infarction, apoplexy, hepatic cirrhosis, cholesterol accumulation, reduced resistance to infections, gout, cancer, hard labor, mellitus diabetes, blemish, anemia, depilation, respiratory disorders, indigestion, cardiopathy, gray hair, swelling, wrinkle, skin sagging, hypothyroidism, depression, irregular periods, hypotonic bladder based on sensory decrease of the bladder or hypotonic bladder accompanied by sensory paralysis of the bladder after surgery of the pelvic viscera, or constipation (preferably constipation).

[66] A method of preventing/treating (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises promoting (I) the binding property of a cholesterol metabolism-related substance to a G protein-coupled receptor protein comprising the same or substantially the same amino acid sequence as the amino acid sequence represented by SEQ ID NO: 1, or a salt thereof, or (II) the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof.

[67] A method of preventing/treating (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises increasing the expression level of a G protein-coupled receptor protein comprising the same or substantially the same amino acid sequence as the amino acid sequence represented by SEQ ID NO: 1, or a salt thereof.

[68] A method of preventing/treating (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises administering to a mammal an effective dose of (i) a G protein-coupled receptor protein comprising the same or substantially the same amino acid sequence as the amino acid sequence represented by SEQ ID NO: 1, a partial peptide thereof, or a salt thereof, (ii) a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an agonist of a G protein-coupled receptor protein comprising the same or substantially the same amino acid sequence as the amino acid sequence represented by SEQ ID NO: 1, or a salt thereof, or (iv) a compound or its salt that increases the expression level of a G protein-coupled receptor protein comprising the same or substantially the same amino acid sequence as the amino acid sequence represented by SEQ ID NO: 1, or a partial peptide thereof.

[69] Use of (i) a G protein-coupled receptor protein comprising the same or substantially the same amino acid sequence as the amino acid sequence represented by SEQ ID NO: 1, a partial peptide thereof, or a salt thereof, (ii) a polynucleotide comprising a polynucleotide encoding a G protein-coupled receptor protein comprising the same or substantially the same amino acid sequence as the amino acid sequence represented by SEQ ID NO: 1, or a partial peptide thereof, (iii) an agonist of a G protein-coupled receptor protein comprising the same or substantially the same amino acid sequence as the amino acid sequence represented by SEQ ID NO: 1, or a salt thereof, or (iv) a compound or its salt that increases the expression level of a G protein-coupled receptor protein comprising the same or substantially the same amino acid sequence as the amino acid sequence represented by SEQ ID NO: 1, or a partial peptide thereof, to manufacture a preventive/therapeutic agent (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof.

[70] A method of preventing/treating (a) a disease associated with dysfunction of a G protein-coupled receptor protein comprising the same or substantially the same amino acid sequence as the amino acid sequence represented by SEQ ID NO: 1, or a salt thereof; (b) a disease caused by inhibiting or reducing the binding of a cholesterol metabolism-related substance to a G protein-coupled receptor protein comprising the same or substantially the same amino acid sequence as the amino acid sequence represented by SEQ ID NO: 1, or a salt thereof; or (c) a disease caused by inhibiting the signal transduction induced by the binding of a cholesterol metabolism-related substance to a G protein-coupled receptor protein comprising the same or substantially the same amino acid sequence as the amino acid sequence represented by SEQ ID NO: 1, or a salt thereof, which comprises potentiating the signal transduction caused by binding of a G protein-coupled receptor protein comprising the same or substantially the same amino acid sequence as the amino acid sequence represented by SEQ ID NO: 1, or a salt thereof, using a cholesterol metabolism-related substance.

BRIEF DESCRIPTION OF THE DRAWINGS

FIG. 2 shows tissue distribution of GPR39 niRNA in rat by RT-PCR, wherein copies/25 ng RNA indicates the copy number per 25 ng of total RNA.

BEST MODE FOR CARRYING OUT THE INVENTION

Figure 1:
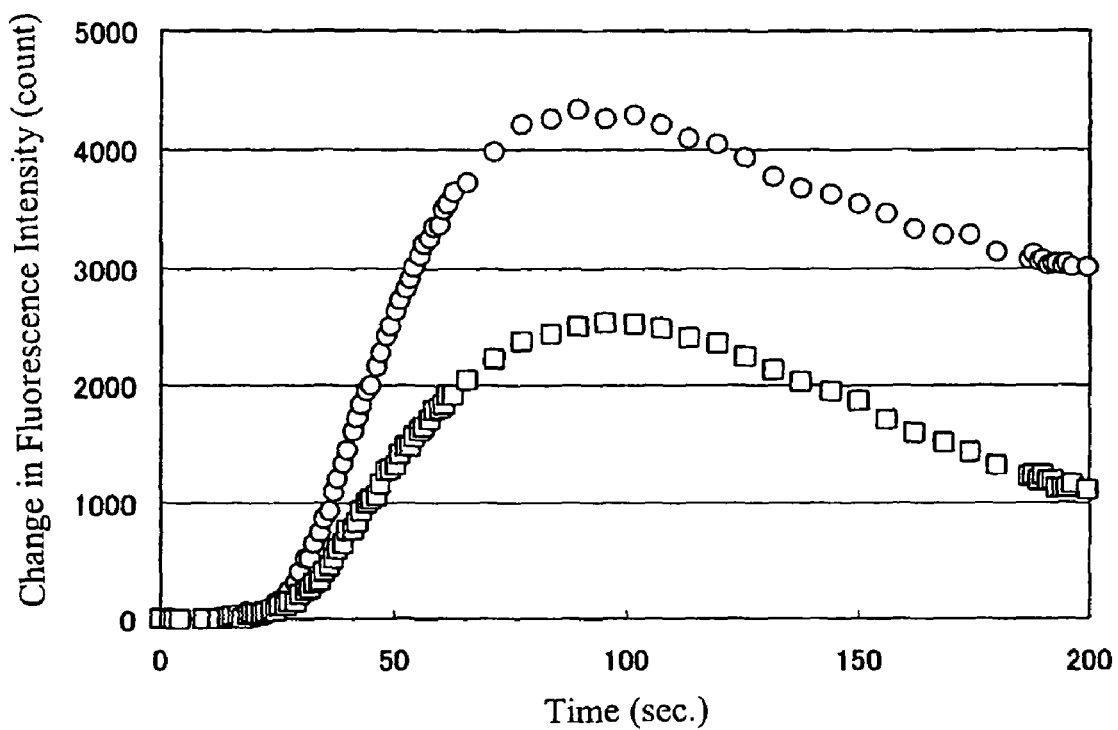
FIG. 1 shows the results obtained by monitoring the changes in intracellular calcium level when taurolithocholic acid was added to rat GPR39 expression vector-transfected CHO cell line (CHO/rGPR39). Symbol ○ (open circle) designates the results when 50 μM taurolithocholic acid was added and Symbol □ (open square) designates the results when 10 μM taurolithocholic acid was added.

The G protein-coupled receptor protein GPR39 used in the present invention (hereinafter sometimes referred to as the GPR39) is a receptor protein comprising the same or substantially the same amino acid sequence as the amino acid sequence represented by SEQ ID NO: 1.

The GPR39 may be any protein derived from any cell of human and mammals (e.g., guinea pig, rat, mouse, rabbit, swine, sheep, bovine, monkey, etc.); any cell (e.g., splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.) or hematocyte type cells; or any tissues where such cells are present, such as brain or any of brain regions (e.g., olfactory bulb, amygdaloid nucleus, basal ganglia, hippocampus, thalamus, hypothalamus, subthalamic nucleus, cerebral cortex, medulla oblongata, cerebellum, occipital pole, frontal lobe, temporal lobe, putamen, caudate nucleus, corpus callosum, substantia nigra), spinal cord, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, peripheral blood cells, prostate, testicle, testis, ovary, placenta, uterus, bone, joint, skeletal muscle, etc.; the proteins may also be synthetic proteins.

The amino acid sequence which is substantially the same as the amino acid sequence represented by SEQ ID NO: 1 includes an amino acid sequence having about 80% or more homology, preferably about 90% or more homology and more preferably about 95% or more homology, to the amino acid sequence represented by SEQ ID NO: 1; etc.

Examples of the protein which comprises substantially the same amino acid sequence as the amino acid sequence represented by SEQ ID NO: 1 of the present invention preferably include a protein having substantially the same amino acid sequence as the amino acid sequence represented by SEQ ID NO: 1 and having the activity substantially equivalent to a protein comprising the amino acid sequence represented by SEQ ID NO: 1, and so on.

Homology of the amino acid sequences can be measured under the following conditions (an expectation value =10; gaps are allowed; matrix=BLOSUM62; filtering=OFF) using a homology scoring algorithm NCBI BLAST (National Center for Biotechnology Information Basic Local Alignment Search Tool).

Examples of the substantially equivalent activity described above include a ligand binding activity, a signal transduction activity, etc. The term substantially equivalent is used to mean that the activities are the same in nature. Therefore, although it is preferred that activities such as the ligand binding and signal transduction activities, etc. be equivalent (e.g., about 0.01- to about 100-fold, preferably about 0.5- to about 20-fold, more preferably about 0.5- to about 2-fold), quantitative factors such as a level of these activities, a molecular weight of the protein, etc. may differ.

The activities such as ligand binding and signal transduction activities or the like can be determined according to publicly known methods with some modifications thereof, for example, by the screening methods that will be later described.

Also, proteins comprising the following amino acid sequences are used as the GPR39: a) amino acid sequences wherein 1 or 2 or more amino acids (preferably approximately 1 to 30 amino acids, more preferably approximately 1 to 10 amino acids, most preferably several (1 to 5) amino acids) are deleted of the amino acid sequence represented by SEQ ID NO: 1, SEQ ID NO: 3 or SEQ ID NO: 5; b) amino acid sequences wherein 1 or 2 or more amino acids (preferably approximately 1 to 30 amino acids, more preferably approximately 1 to 10 amino acids, and most preferably several (1 to 5) amino acids) are added to the amino acid sequence represented by SEQ ID NO: 1, SEQ ID NO: 3 or SEQ ID NO: 5; c) amino acid sequences wherein 1 or 2 or more amino acids (preferably approximately 1 to 30 amino acids, more preferably approximately 1 to 10 amino acids, and most preferably several (1 to 5) amino acids) in the amino acid sequence represented by SEQ ID NO: 1, SEQ ID NO: 3 or SEQ ID NO: 5 are substituted by other amino acids; or d) combination of these amino acid sequences described above; and the like.

Throughout the present specification, the GPR39 is represented in accordance with the conventional way of describing peptides, that is, the N-terminus (amino terminus) at the left hand and the C-terminus (carboxyl terminus) at the right hand. In the GPR39 including proteins comprising the amino acid sequence shown by SEQ ID NO: 1, the C-terminus may be in any form of a carboxyl group (—COOH), carboxylate (—COO−), an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; and the like. In addition, pivaloyloxymethyl or the like, which is used widely as an ester for oral administration, may also be used.

Where the GPR39 contains a carboxyl group (or a carboxylate) at a position other than the C-terminus, it may be amidated or esterified and such an amide or ester is also included within the GPR39 defined in the present invention. The ester group may be the same group as that described with respect to the C-terminus described above.

Furthermore, examples of the GPR39 include variants of the above proteins, wherein the amino group at the N-terminal methionine residue of the protein supra is protected with a protecting group (for example, a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

As specific examples of the GPR39, there are employed, for example, human-derived GPR39 consisting of the amino acid sequence represented by SEQ ID NO: 1, mouse-derived GPR39 consisting of the amino acid sequence represented by SEQ ID NO: 3, rat-derived GPR39 consisting of the amino acid sequence represented by SEQ ID NO: 5, and the like. Human-derived GPR39 is a publicly known protein described in Genomics, 1997 Dec. 15, 46(3): 426-34; and in WO 2002/61087, US 2002/004491, WO 2002/39885, WO 2002/71928, WO 2001/81634, WO 2002/79492 and WO 2002/86443.

As the partial peptide of the GPR39 (hereinafter sometimes referred to as the partial peptide), any partial peptide can be used so long as it is a peptide having a part of the amino acid sequence of the GPR39 described above. For example, among protein molecules of the GPR39, those having a site exposed to the outside of a cell membrane and having substantially the same receptor binding activity as in the GPR39 can be used.

Specifically, the partial peptide of the GPR39 having the amino acid sequence represented by SEQ ID NO: 1, SEQ ID NO: 3 or SEQ ID NO: 5 is a peptide containing the parts analyzed to be extracellular domains (hydrophilic domains) in the hydrophobic plotting analysis. A peptide containing the hydrophobic domain in part can be used as well. In addition, the peptide may contain each domain separately or plural domains together.

In the partial peptides of the present invention, preferred are peptides having at least 20, preferably 50 or more, and more preferably 100 or more amino acids, in the amino acid sequence which constitutes the receptor protein of the present invention described above.

The amino acid sequence having substantially the same amino acid sequence includes an amino acid sequence having at least about 80% homology, preferably 85% or more homology, more preferably about 90% or more homology and furthermore preferably about 95% or more homology, to these amino acid sequences.

Homology of the amino acid sequences can be measured under the same conditions using the same homology scoring algorithm NCBI BLAST as described above.

Herein the term "substantially the same receptor binding activity" has the same significance as described above. The "substantially the same receptor binding activity" can be assayed by the same manner as described above.

In the amino acid sequence described above, the partial peptide of the present invention may contain amino acid sequences, of which 1 or 2 or more amino acids (preferably approximately 1 to 10 amino acids, more preferably several (1 to 5) amino acids) are deleted; to which 1 or 2 or more amino acids (preferably approximately 1 to 20 amino acids, more preferably approximately 1 to 10 amino acids, and most preferably several (1 to 5) amino acids) are added; or, in which 1 or 2 or more amino acids (preferably approximately 1 to 10 amino acids, more preferably several and most preferably approximately 1 to 5 amino acids) are substituted by other amino acids.

In the partial peptide of the present invention, the C-terminus may be in any form of a carboxyl group (—COOH), carboxylate (—COO−), an amide (—CONH$_2$) or an ester (—COOR). Where the partial peptide of the present invention contains a carboxyl group (or a carboxylate) at a position other than the C-terminus, it may be amidated or esterified and such an amide or ester is also included within the partial peptide of the present invention. In this case, the ester group may be the same group as that described with respect to the C-terminus described above.

As in the GPR39 described above, the partial peptide of the present invention further includes those in which the amino group of the amino acid residue of the N-terminal methionine residue is protected by a protecting group, those in which the N-terminal residue is cleaved in vivo and the produced glutamine residue is pyroglutaminated, those in which substituents on the side chains of amino acids in the molecule are protected by appropriate protecting groups, conjugated peptides such as so-called glycopeptides, to which sugar chains are bound, and the like.

For salts of the GPR39 or its partial peptide, preferred are physiologically acceptable salts with acids or bases, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The GPR39 or its salts may be manufactured by a publicly known method used to purify receptor proteins from human or mammalian cells or tissues described above, or by culturing a transformant that contains the DNA encoding the GPR39, as will be later described. Furthermore, the GPR39 or its salts may also be manufactured by the methods for synthesizing proteins or by modifications thereof, which will also be described hereinafter.

Where the GPR39 or its salts are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the GPR39 or its partial peptides, or salts or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmehtylphenyl acetamidomethyl resin, polyacrylamide resin, 4-(2',4'-dimethoxyphenylhydroxymethyl)phenoxy resin, 4-(2',4'-dimethoxyphenyl-Fmoc-aminoethyl)phenoxy resin, etc. Using these resins, amino acids in which α-amino groups and functional groups on the side chains are appropriately protected are condensed on the resin in the order of the sequence of the objective protein according to various condensation methods publicly known in the art. At the end of the reaction, the protein is cut out from the resin and at the same time, the protecting groups are removed. Then, intramolecular disulfide bond-forming reaction is performed in a highly diluted solution to obtain the objective protein or its amides.

For condensation of the protected amino acids described above, a variety of activation reagents for protein synthesis may be used, and carbodiimides are particularly preferable. Examples of such carbodiimides include DCC, N,N'-diisopropylcarbodiimide, N-ethyl-N'-(3-dimethylaminoprolyl) carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately −20 to 50° C. The activated amino acid derivatives are used generally in an excess of 1.5 to 4 times. The condensation is examined by a test using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the amino groups of the starting compounds include Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br—Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups used in the starting compounds include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc.

As the activated amino acids, in which the amino groups are activated in the starting material, for example, the corresponding phosphoric amides are employed.

To eliminate (split off) the protecting groups, there are used catalytic reduction under hydrogen gas flow in the presence of a catalyst such as Pd-black, Pd-carbon, etc.; an acid treatment with anhydrous hydrogen fluoride, methanesulfonic acid, trifluoromethane-sulfonic acid or trifluoroacetic acid, or a mixture solution of these acids; a treatment with a base such as diisopropylethylamine, triethylamine, piperidine, piperazine, etc.; and reduction with sodium in liquid ammonia. The elimination of the protecting group by the acid treatment described above is carried out generally at a temperature of approximately −20 to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, elimination of the protecting groups, activation of functional groups involved in the reaction, or the like may be appropriately selected from publicly known groups and publicly known means.

In another method for obtaining the amides of the protein, for example, the α-carboxyl group of the carboxy terminal amino acid is first protected by amidation; the peptide (protein) chain is then extended from the amino group side to a desired length. Thereafter, a protein in which only the protecting group of the N-terminal α-amino group in the peptide chain has been eliminated from the protein and a protein in which only the protecting group of the C-terminal carboxyl group has been eliminated are prepared. The two proteins are condensed in a mixture of the solvents described above. The details of the condensation reaction are the same as described above. After the protected protein obtained by the condensation is purified, all the protecting groups are eliminated by the method described above to give the desired crude protein. This crude protein is purified by various known purification means. Lyophilization of the major fraction gives the amide of the desired protein.

To prepare the esterified protein, for example, the α-carboxyl group of the carboxy terminal amino acid is condensed with a desired alcohol to prepare the amino acid ester, which is followed by procedure similar to the preparation of the amidated protein above to give the ester form of the desired protein.

The partial peptide of the GPR39, or a salt thereof can be manufactured by publicly known methods for peptide synthesis, or by cleaving the GPR39 with an appropriate peptidase. For the methods for peptide synthesis, for example, either solid phase synthesis or liquid phase synthesis may be used. That is, the partial peptide or amino acids that can construct the GPR39 are condensed with the remaining part. Where the product contains protecting groups, these protecting groups are removed to give the desired peptide. Publicly known methods for condensation and elimination of the protecting groups are described in a)-e) below.

a) M. Bodanszky & M. A. Ondetti: Peptide Synthesis, Interscience Publishers, New York (1966)

b) Schroeder & Luebke: The Peptide, Academic Press, New York (1965)

c) Nobuo Izumiya, et al.: *Peptide Gosei-no-Kiso to Jikken* (Basics and experiments of peptide synthesis), published by Maruzen Co. (1975)

d) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

e) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the partial peptide of the present invention. When the partial peptide obtained by the methods above is in a free form, the peptide can be converted into an appropriate salt by a publicly known method; conversely when the peptide is obtained in a salt form, it can be converted into a free form by a publicly known method.

The polynucleotide encoding the GPR39 may be any polynucleotide so long as it contains the base sequence (DNA or RNA, preferably DNA) encoding the GPR39 described above. Such a polynucleotide may also be any one of DNA encoding the GPR39, or RNA such as mRNA, etc. and may be double-stranded or single-stranded.

Where the polynucleotide is double-stranded, it may be double-stranded DNA, double-stranded RNA or DNA:RNA hybrid. Where the polynucleotide is single-stranded, it may be a sense strand (i.e., a coding strand) or an antisense strand (i.e., a non-coding strand).

Using the polynucleotide encoding the GPR39, mRNA of the GPR39 can be quantified by, for example, the publicly known method published in separate volume of *Jikken Igaku* 15 (7) "New PCR and its application" (1997), or by its modifications.

The DNA encoding the GPR39 may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding the GPR39 may be any DNA, so long as it is, for example, a DNA comprising the base sequence represented by SEQ ID NO: 2, or any DNA having a base sequence hybridizable to the base sequence represented by SEQ ID NO: 2 under high stringent conditions and encoding a receptor protein which has the activities substantially equivalent to those of the GPR39 (e.g., the ligand-binding activities, the signal transduction activities, etc.).

Examples of the DNA hybridizable to the DNA comprising the base sequence represented by SEQ ID NO: 2 under highly stringent conditions include a DNA comprising a base sequence having about 80% or more homology, preferably about 90% or more homology and more preferably about 95% or more homology, to the base sequence represented by SEQ ID NO: 2.

Homology of the base sequences can be measured under the following conditions (an expectation value=10; gaps are allowed; filtering=ON, match Score=1, mismatch Score=−3) using a homology scoring algorithm NCBI BLAST (National Center for Biotechnology Information Basic Local Alignment Search Tool).

The hybridization can be carried out by publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding human-derived GPR39 consisting of the amino acid sequence represented by SEQ ID NO: 1, there may be employed a DNA consisting of the base sequence represented by SEQ ID NO: 2; etc. As the DNA encoding mouse-derived GPR39 consisting of the amino acid sequence represented by SEQ ID NO: 6, there may be employed a DNA consisting of the base sequence represented by SEQ ID NO: 7; etc. As the DNA encoding rat-derived GPR39 consisting of the amino acid sequence represented by SEQ ID NO: 8, there may be employed a DNA consisting of the base sequence represented by SEQ ID NO: 9; etc.

The term polynucleotide comprising a part of the base sequence of the DNA encoding the GPR39 or a part of the base sequence complementary to the DNA is used to mean that the polynucleotide embraces not only the DNA encoding the partial peptide of the present invention described below but also RNA.

According to the present invention, antisense polynucleotides (nucleic acids) that can inhibit the replication or expression of the GPR39 gene can be designed and synthesized based on the base sequence information of the cloned or determined DNA encoding the GPR39. Such a polynucleotide (nucleic acid) is capable of hybridizing to RNA of the GPR39 gene to inhibit the synthesis or function of said RNA or capable of modulating or controlling the expression of the GPR39 gene via interaction with the GPR39-associated RNA. Polynucleotides complementary to the selected sequences of RNA associated with the GPR39 of the invention and polynucleotides specifically hybridizable to RNA associated with the GPR39 of the invention are useful in modulating or controlling the expression of the GPR39 gene in vivo and in vitro, and useful for the treatment or diagnosis of diseases. The term "corresponding" is used to mean homologous to or complementary to a particular sequence of the nucleotide, base sequence or nucleic acid including the gene. The term "corresponding" between nucleotides, base sequences or nucleic acids and peptides (proteins) usually refer to amino acids of a peptide (protein) under the order derived from the sequence of nucleotides (nucleic acids) or their complements. In the genes for the GPR39, the 5' end hairpin loop, 5' end 6-base-pair repeats, 5' end untranslated region, polypeptide translation initiation codon, protein coding region, ORF translation initiation codon, 3' end untranslated region, 3' end palindrome region, and 3' end hairpin loop, may be selected as preferred target regions, though any other region may be selected as a target in the gene for the GPR39.

The relationship between the targeted nucleic acids and the polynucleotides complementary to at least a part of the target, specifically the relationship between the target and the polynucleotides hybridizable to the target, can be denoted to be "antisense." Examples of the antisense polynucleotides include polydeoxyribonucleotide containing 2-deoxy-D-ribose, polyribonucleotide containing D-ribose, any other type of polynucleotides which are N-glycosides of a purine or pyrimidine base or other types, or other polymers containing non-nucleotide backbones (e.g., commercially available protein nucleic acids and synthetic sequence-specific nucleic acid polymers) or other polymers containing special linkages (provided that the polymers contain nucleotides having such a configuration that allows base pairing or base stacking, as is found in DNA or RNA), etc. They may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., α anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cellular permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense nucleic acid of the present invention may contain changed or modified sugars, bases or linkages. The antisense nucleic acid may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof(e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleic acid can be examined using the transformant of the present invention, the gene expression system of the present invention in vivo and in vitro, or the translation system of the G protein-coupled receptor protein in vivo and in vitro. The nucleic acid can be applied to cells by a variety of publicly known methods.

The DNA encoding the partial peptide of the present invention may be any DNA so long as it contains the base sequence encoding the partial peptide of the present invention described above. The DNA may also be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using mRNA fraction prepared from the cells and tissues described above.

Specifically, the DNA encoding the partial peptide of the present invention may be any one of, for example, (1) a DNA having a partial base sequence of the DNA having the base sequence represented by SEQ ID NO: 2, or (2) any DNA having a partial base sequence of the DNA having a base sequence hybridizable to the base sequence represented by SEQ ID NO: 2 under highly stringent conditions and encoding the receptor protein which has the activities (e.g., the ligand-biding activities, the signal transduction activities, etc.) substantially equivalent to those of the GPR39; etc.

Examples of the DNA that is hybridizable to the base sequence represented by SEQ ID NO: 2 include a DNA comprising a base sequence having about 80% or more homology, preferably about 90% or more homology and more preferably about 95% or more homology, to the base sequence represented by SEQ ID NO: 2.

Homology of the amino acid sequences can be measured under the same conditions using the same homology scoring algorithm NCBI BLAST as described above.

The method and conditions of hybridization are the same as described above.

For cloning of the DNA that completely encodes the GPR39 or its partial peptide (hereinafter sometimes collectively referred to as the GPR39), the DNA may be amplified by PCR using synthetic DNA primers containing a part of the base sequence of the GPR39, or the DNA inserted into an appropriate vector can be selected by hybridization with a labeled DNA fragment or synthetic DNA that encodes a part or entire region of the GPR39. The hybridization can be carried out, for example, according to the method described in Molecular Cloning, 2nd, J. Sambrook et al., Cold Spring Harbor Lab. Press, 1989. The hybridization may also be performed using commercially available library in accordance with the protocol described in the attached instructions.

Conversion of the base sequence of the DNA can be effected by publicly known methods such as the ODA-LA PCR method, the Gapped duplex method or the Kunkel method or its modifications by using publicly known kits available as Mutan™-superExpress Km (manufactured by TaKaRa Shuzo Co., Ltd.), Mutan™-K (manufactured by TaKaRa Shuzo Co., Ltd.), etc.

The cloned DNA encoding the GPR39 can be used as it is, depending upon purpose or, if desired, after digestion with a restriction enzyme or after addition of a linker thereto. The DNA may contain ATG as a translation initiation codon at the 5' end thereof and may further contain TAA, TGA or TAG as a translation termination codon at the 3' end thereof These translation initiation and termination codons may also be added by using an appropriate synthetic DNA adapter.

The expression vector for the GPR39 can be manufactured, for example, by (a) excising the desired DNA fragment from the DNA encoding the GPR39, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, CMV promoter or SRα promoter is preferably used. Where the host is bacteria of the genus *Escherichia*, preferred examples of the promoter include trp promoter, lac promoter, recA promoter, $\lambda P_L$ promoter, lpp promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a polyA addition signal, a selection marker, SV40 replication origin (hereinafter sometimes abbreviated as SV40ori) etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker in CHO (dhfr⁻) cells, selection can also be made on thymidine free media.

If necessary, a signal sequence that matches with a host is added to the N-terminus of the receptor protein of the present invention. Examples of the signal sequence that can be used are PhoA signal sequence, OmpA signal sequence, etc. in the case of using bacteria of the genus *Escherichia* as the host; α-amylase signal sequence, subtilisin signal sequence, etc. in the case of using bacteria of the genus *Bacillus* as the host; MFα signal sequence, SUC2 signal sequence, etc. in the case of using yeast as the host; and insulin signal sequence, α-interferon signal sequence, antibody molecule signal sequence, etc. in the case of using animal cells as the host, respectively.

Using the vector containing the DNA encoding the GPR39 thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris*, etc.

Examples of insect cells include, for the virus AcNPV, *Spodoptera frugiperda* cells (Sf cells), MG1 cells derived from mid-intestine of *Trichoplusia ni*, High Five™ cells derived from egg of *Trichoplusia ni*, cells derived from *Mamestra brassicae*, cells derived from *Estigmena acrea*, etc.; and for the virus BmNPV, *Bombyx mori* N cells (BmN cells), etc. are used. Examples of the Sf cell which can be used are Sf9 cells (ATCC CRL1711) and Sf21 cells (both cells are described in Vaughn, J. L. et al., In Vivo, 13, 213-217 (1977)).

As the insect, for example, a larva of *Bombyx mori* can be used [Maeda, et al., Nature, 315, 592 (1985)].

Examples of animal cells include monkey cells COS-7, Vero, Chinese hamster cells CHO (hereinafter referred to as CHO cells), dhfr gene deficient Chinese hamster cells CHO (hereinafter briefly referred to as CHO (dhfr⁻) cell), mouse L cells, mouse AtT-20, mouse myeloma cells, rat GH3, human FL cells, human HEK293 cells, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55(1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995) (published by Shujunsha), or Virology, 52, 456 (1973).

Thus, the transformant transformed with the expression vector containing the DNA encoding the GPR39 can be obtained.

Where the host is bacteria belonging to the genus *Escherichia* or the genus *Bacillus*, the transformant can be appropriately incubated in a liquid medium which contains materials required for growth of the transformant such as carbon sources, nitrogen sources, inorganic materials, and so on. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extract, vitamins, growth promoting factors etc. may also be added to the medium. Preferably, pH of the medium is adjusted to about 5 to about 8.

A preferred example of the medium for incubation of the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary and desired, the culture can be aerated or agitated.

Where animal cells are employed as the host, the transformant is cultivated in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary and desired, the culture can be aerated or agitated.

As described above, the GPR39 can be produced into the cell, in the cell membrane or out of the cell of the transformant.

The GPR39 can be separated and purified from the culture described above by the following procedures.

When the GPR39 is extracted from the culture or cells, after cultivation the transformants or cells are collected by a publicly known method and suspended in a appropriate buffer. The transformants or cells are then disrupted by publicly known methods such as ultrasonication, a treatment with lysozyme and/or freeze-thaw cycling, followed by centrifugation, filtration, etc. Thus, the crude extract of the GPR39 can be obtained. The buffer used for the procedures may contain a protein modifier such as urea or guanidine hydrochloride, or a surfactant such as Triton X-100™, etc. When the GPR39 is secreted in the culture, after completion of the cultivation the supernatant can be separated from the transformants or cells to collect the supernatant by a publicly known method.

The GPR39 contained in the supernatant or the extract thus obtained can be purified by appropriately combining the publicly known methods for separation and purification. Such publicly known methods for separation and purification include a method utilizing difference in solubility such as salting out, solvent precipitation, etc.; a method utilizing mainly difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

In the case that the GPR39 thus obtained is in a free form, it can be converted into the salt by publicly known methods or modifications thereof On the other hand, when the GPR39 is obtained in the form of a salt, it can be converted into the free form or in the form of a different salt by publicly known methods or modifications thereof. The GPR39 produced by the recombinant can be treated, prior to or after the purification, with an appropriate protein modifying enzyme so that the GPR39 can be appropriately modified to partially remove a polypeptide. Examples of the protein-modifying enzyme include trypsin, chymotrypsin, arginyl endopeptidase, protein kinase, glycosidase or the like.

The activity of the thus produced the GPR39 can be determined by a binding experiment to a labeled ligand, by an enzyme immunoassay using a specific antibody, or the like.

Antibodies to the GPR39 may be any of polyclonal antibodies and monoclonal antibodies, as long as they are capable of recognizing the GPR39.

The antibodies to the GPR39 may be manufactured by publicly known methods for manufacturing antibodies or antisera, using as antigens the GPR39.

[Preparation of Monoclonal Antibody]

(a) Preparation of Monoclonal Antibody-Producing Cells

The GPR39 is administered to mammals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once in every two to six weeks and 2 to 10 times in total. Examples of the applicable mammals are monkeys, rabbits, dogs, guinea pigs, mice, rats, sheep and goats, with mice and rats being preferred.

In the preparation of monoclonal antibody-producing cells, warm-blooded animals, e.g., mice, immunized with an antigen wherein the antibody titer is noted is selected, then the spleen or lymph node is collected after 2 to 5 days from the final immunization and antibody-producing cells contained therein are fused with myeloma cells to give monoclonal antibody-producing hybridomas. Measurement of the antibody titer in antisera may be made, for example, by reacting a labeled form of the receptor protein, which will be described later, with the antiserum followed by assaying the binding activity of the labeling agent bound to the antibody. The fusion may be operated, for example, by the known Koehler and Milstein method [Nature, 256, 495 (1975)]. Examples of the fusion accelerator are polyethylene glycol (PEG), Sendai virus, etc., of which PEG is preferably employed.

Examples of the myeloma cells are NS-1, P3U1, SP2/0, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubating at about 20 to about 40° C., preferably at about 30 to about 37° C. for about 1 to about 10 minutes, an efficient cell fusion can be carried out.

Various methods can be used for screening of a monoclonal antibody-producing hybridoma. Examples of such methods include a method which comprises adding the supernatant of hybridoma to a solid phase (e.g., microplate) adsorbed with an antigen of the receptor protein directly or together with a carrier, adding an anti-immunoglobulin antibody (when mouse cells are used for the cell fusion, anti-mouse immunoglobulin antibody is used) labeled with a radioactive substance or an enzyme, or Protein A and detecting the monoclonal antibody bound to the solid phase, and a method which comprises adding the supernatant of hybridoma to a solid phase adsorbed with an anti-immunoglobulin antibody or Protein A, adding the receptor protein labeled with a radioactive substance or an enzyme and detecting the monoclonal antibody bound to the solid phase.

The monoclonal antibody can be selected by publicly known methods or by modifications of these methods. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1% to 20%, preferably 10% to 20% fetal bovine serum, GIT medium (Wako Pure Chemical Industries, Ltd.) containing 1% to 10% fetal bovine serum, a serum free medium for cultivation of a hybridoma (SFM-101, Nissui Seiyaku Co., Ltd.) and the like can be used for the selection and growth medium. The cultivation is carried out generally at 20° C. to 40° C., preferably at about 37° C., for 5 days to 3 weeks, preferably 1 to 2 weeks. The cultivation can be conducted normally in 5% $CO_2$. The antibody titer of the culture supernatant of hybridomas can be determined as in the assay for the antibody titer in antisera described above.

(b) Purification of Monoclonal Antibody

Separation and purification of a monoclonal antibody can be carried out by methods applied to conventional separation and purification of immunoglobulins, as in the conventional methods for separation and purification of polyclonal antibodies [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A, Protein G, etc. and dissociating the binding to obtain the antibody].

[Preparation of Polyclonal Antibody]

The polyclonal antibody of the present invention can be manufactured by publicly known methods or modifications thereof. For example, a complex of immunogen (the GPR39 as an antigen) and a carrier protein is prepared, and a mammal is immunized with the complex in a manner similar to the method described above for the manufacture of monoclonal antibodies. The product containing the antibody to the GPR39 is collected from the immunized animal followed by separation and purification of the antibody.

In the complex of an immunogen and a carrier protein used to immunize a mammal, the type of carrier protein and the mixing ratio of a carrier to hapten may be any type and in any ratio, as long as the antibody is efficiently produced to the hapten immunized by crosslinking to the carrier. For example, bovine serum albumin, bovine thyroglobulins, keyhole limpet hemocyanin, etc. is coupled to hapten in a carrier-to-hapten weight ratio of approximately 0.1 to 20, preferably about 1 to about 5.

A variety of condensing agents can be used for the coupling of a carrier to hapten. Glutaraldehyde, carbodiimide, maleimide activated ester, activated ester reagents containing thiol group or dithiopyridyl group, etc. are used for the coupling.

The condensation product is administered to warm-blooded animals either solely or together with carriers or diluents to the site in which the antibody can be produced by the administration. In order to potentiate the antibody productivity upon the administration, complete Freund's adjuvant or incomplete Freund's adjuvant may be administered. The administration is usually made once approximately in every 2 to 6 weeks and about 3 to about 10 times in total.

The polyclonal antibody can be collected from the blood, ascites, etc., preferably from the blood of mammals immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as applied to the separation and purification of monoclonal antibodies described hereinabove.

One type of the ligands for GPR39 is a cholesterol metabolism-related substance and specific examples include bile acids (e.g., taurolithocholic acid, glycolithocholic acid, taurodeoxycholic acid, glycodeoxycholic acid, nordeoxycholic acid, 7-ketolithocholic acid, 5β-pregnan-3,20-one, cholic acid, lithocholic acid, deoxycholic acid, taurocholic acid, glycocholic acid, chenodeoxycholic acid, ursodeoxycholic acid, taurochenodeoxycholic acid, glycochenodeoxycholic acid, epiandrosterone, (+)-4-androsterone-3,17-dione, cis-androsterone, 11β-hydroxyprogesterone, 17α-hydroxyprogesterone, 11-deoxycorticosterone, 11-deoxycortisol, dehydroisoandrosterone, 3α-hydroxy-5α-pregnan-20-one, 4-pregnen-20α-ol-3-one, 5α-dehydrotestosterone, testosterone, progesterone, or salts thereof, etc. Bile acids are preferably used and particularly preferred is taurolithocholic acid.

Therefore, GPR39, the DNA encoding the GPR39 (hereinafter sometimes referred to briefly as the DNA of the present invention), the antibody to the GPR39 (hereinafter sometimes referred to briefly as the antibody of the present invention) and the antisense DNA to the DNA of the present invention (hereinafter sometimes merely referred to as the antisense DNA of the present invention) have the following applications.

(1) Preventive/Therapeutic Agent for Diseases Associated with Dysfunction of the GPR39 a) The GPR39 or b) the DNA encoding the GPR39 can be used as a preventive/therapeutic agent, etc. for diseases associated with dysfunction of the GPR39.

For example, when the physiological activities of the cholesterol metabolism-related substance, which is the ligand, cannot be expected in a patient (deficiency of the GPR39) due to a decrease of the GPR39 in the body, the amount of the GPR39 can be increased in the boy of the patient a) by administering the GPR39 to the patient thereby to supplement the amount of the GPR39; or b) (i) by administering the DNA encoding the GPR39 to the patient and expressing the same, or (ii) by inserting and expressing the DNA encoding the GPR39 in the objective cells and then transplanting the cells to the patient, thus increasing the amount of the GPR39 in the body of the patient, whereby the activities of the ligand can be sufficiently exhibited. That is, the DNA encoding the GPR39 is useful as a safe and low toxic preventive/therapeutic agent for diseases associated with dysfunction of the GPR39.

Diseases associated with dysfunction of the GPR39, for which the agonist of the GPR39 (preferably the agonist that potentiates the signal transduction induced by the binding of the cholesterol metabolism-related protein to the GPR39) is useful, include, for example, growth retardation, lacerations, burn injury, poor circulation, decline in learning ability, hypogonadism, dysgeusia, anosmia, hyperplasia, arteriosclerosis, myocardial infarction, apoplexy, hepatic cirrhosis, cholesterol accumulation, reduced resistance to infections, gout, cancer, hard labor, mellitus diabetes, blemish, anemia, depilation, respiratory disorders, indigestion, cardiopathy, gray hair, swelling, wrinkle, skin sagging, hypothyroidism, depression, irregular periods, hypotonic bladder based on sensory decrease of the bladder or hypotonic bladder accompanied by sensory paralysis of the bladder after surgery of the pelvic viscera, or constipation (preferably constipation), or the like.

When the GPR39 is used as the preventive/therapeutic agent described above, the GPR39 can be prepared into a pharmaceutical composition in a conventional manner.

On the other hand, where the DNA of the present invention is used as t the pharmaceuticals described above, the DNA itself is administered; alternatively, the DNA is inserted into an appropriate vector such as retrovirus vector, adenovirus vector, adenovirus-associated virus vector, etc. and then administered in a conventional manner. The DNA of the present invention may also be administered as naked DNA, or with adjuvants to assist its uptake by gene gun or through a catheter such as a catheter with a hydrogel.

For example, a) the GPR39 or b) the DNA of the present invention can be used orally, for example, in the form of tablets which may be sugar coated if necessary, capsules, elixirs, microcapsules etc., or parenterally in the form of injectable preparations such as a sterile solution and a suspension in water or with other pharmaceutically acceptable liquid. These preparations can be manufactured by mixing a) the GPR39 or b) the DNA of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil and cherry. When the unit dosage is in the form of capsules, liquid carriers such as oils and fats may further be used together with the additives described above. A sterile composition for injection may be formulated by conventional procedures used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition. Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate, benzyl alcohol, etc.

The preventive/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the GPR39 varies depending on subject to be administered, target organ, conditions, methods for administration, etc.; in oral administration, the daily dose for the patient with, e.g., disease associated with dysfunction of the GPR39 is normally about 0.1 mg to about 100 mg, preferably about 1.0 to about 50 mg, and more preferably about 1.0 to about 20 mg per day (as 60 kg body weight). In parenteral administration, its single dose varies depending on subject to be administered, target organ, conditions, method for administration, etc., but generally in the form of injectable preparation, the GPR is advantageously administered intravenously to the patient with, e.g., disease associated with dysfunction of the GPR39 in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

The dose of the DNA of the present invention varies depending on subject to be administered, target organ, conditions, method for administration, etc.; in oral administration, the daily dose for the patient with, e.g., disease associated with dysfunction of the GPR39 is normally about 0.1 mg to about 100 mg, preferably about 1.0 to about 50 mg, and more preferably about 1.0 to about 20 mg per day (as 60 kg body weight). In parenteral administration, its single dose varies depending on subject to be administered, target organ, conditions, method for administration, etc., but generally in the form of injectable preparation, the active ingredient is advantageously administered intravenously to the patient with, e.g., disease associated with dysfunction of the GPR39 in a daily dose of about 0.01 to about 30 mg, preferably about 0.1 to about 20 mg, and more preferably about 0.1 to about 10 mg (as 60 kg body weight). For other animal species, the corresponding dose as converted per 60 kg body weight can be administered.

(2) Gene Diagnostic Agent

By using the DNA and antisense DNA of the present invention as probes, abnormalities (gene abnormalities) of the DNA or mRNA encoding the GPR39 or its partial peptides in human or mammals (e.g., rats, mice, rabbits, sheep, swine, bovine, cats, dogs, monkeys, etc.) can be detected, and the DNA and antisense DNA are thus useful as gene diagnostic agents for the damage against the DNA or mRNA, its mutation, or its reduced expression, or increased expression or overexpression of the DNA or mRNA.

The gene diagnosis described above using the DNA or antisense DNA of the present invention can be performed by, for example, the publicly known Northern hybridization assay or the PCR-SSCP assay (Genomics, 5, 874-879 (1989); Proceedings of the National Academy of Sciences of the United States of America, 86, 2766-2770 (1989)), etc.

Where a reduced expression or overexpression of the GPR39 is detected, e.g., by northern hybridization, it can be diagnosed that one suffers from, for example, diseases associated with dysfunction or hyperfunction of the GPR39, or it is highly likely to suffer from these disease in the future.

The diseases associated with hyperfunction of the GPR39 are, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or vomiting which might be induced by functional bowel disorders caused by gastrointestinal motility disturbances, irritable bowel syndrome, fecal incontinence, colitis or Crohn's disease; or the like.

(3) Medicament Comprising the Compound or its Salt that Alters the Expression Level of the GPR39

By using the DNA of the present invention as a probe, the DNA can be used for screening the compound or its salt that alters the expression level of the GPR39.

That is, the present invention provides a method of screening the compound or its salt that alters the expression level of the GPR39, which comprises measuring the amount of mRNA in the GPR39 contained, for example, in (i) a) blood, b) particular organs, c) tissues or cells isolated from the organs of non-human mammals or in (ii) transformants, etc.

The amount of mRNA in the GPR39 can be measured specifically as follows.

(i) Normal or disease models of non-human mammals (e.g., mice, rats, rabbits, sheep, swine, bovine, cats, dogs, monkeys, more specifically, immunodeficiency models of rats, mice, rabbits, etc.) receive administration of a drug (e.g., immunomodulator, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time.

The mRNA of the GPR39 contained in the thus obtained cells is extracted from the cells, for example, in a conventional manner and quantified by means of, e.g., TaqManPCR, or may also be analyzed by northern blot technique by publicly known methods.

(ii) Transformants that express the GPR39 are prepared according to the methods described above, and the mRNA encoding the GPR39 can be quantified and analyzed, as described above.

The compound that alters the expression level of the GPR39 can be screened by the following procedures.

(i) To normal or disease models of non-human mammals, a test compound is administered at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of mRNA encoding the GPR39 contained in cells are quantified and analyzed.

(ii) Transformants are cultured in a conventional manner and a test compound is mixed in the culture medium. After a specified time (after 1 day to 7 days, preferably after 1 day to 3 days, more preferably after 2 to 3 days), the amount of mRNA of the GPR39 contained in the transformants can be quantified and analyzed.

The test compounds used may be peptides, proteins, non-peptide compounds, synthetic compounds, fermentation products, cell extracts, plant extract, animal tissue extracts, plasma, etc. These compounds may be novel or publicly known compounds.

The test compound may form salts, and these salts of the test compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound, which is obtained by the screening methods of the present invention, is the compound that alters the expression level of the GPR39. Specifically, it is (a) the compound that increases the expression level of the GPR39 thereby to potentiate the GPR39-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular protein, activation of c-fos, pH reduction, etc., especially, the compound that potentiates the intracellular $Ca^{2+}$ level increasing activity (intracellular $Ca^{2+}$ releasing activity); and (b) the compound that reduces the expression level of the GPR39 thereby to attenuate those cell-stimulating activities.

The compound, which is obtained by the screening methods of the present invention, includes peptides, proteins, non-peptide compounds, synthetic compounds, fermentation products, etc. They may be novel or known compounds.

As the salts of the compound obtained by the screening methods of the present invention, there may be used salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Accordingly, the compound or its salt that alters the expression level of the GPR39 obtained by the screening method can be used as agents for preventing/treating diseases associated with excessive action of the GPR39 (e.g., (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc.), or as antiemetic agents for vomiting which might be induced by functional bowel disorders caused by gastrointestinal motility disturbances, irritable bowel syndrome, fecal incontinence, colitis or Crohn's disease; or the like.

Specifically, the compound or its salt that decreases the expression level of the GPR39 can be used as agents for preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc.), or as antiemetic agents for vomiting which might be induced by functional bowel disorders caused by gastrointestinal motility disturbances, irritable bowel syndrome, fecal incontinence, colitis or Crohn's disease; or the like.

The compound or its salt that increases the expression level of the GPR39 is useful as an agent for preventing/treating, for example, growth retardation, lacerations, burn injury, poor circulation, decline in learning ability, hypogonadism, dysgeusia, anosmia, hyperplasia, arteriosclerosis, myocardial infarction, apoplexy, hepatic cirrhosis, cholesterol accumulation, reduced resistance to infections, gout, cancer, hard labor, mellitus diabetes, blemish, anemia, depilation, respiratory disorders, indigestion, cardiopathy, gray hair, swelling, wrinkle, skin sagging, hypothyroidism, depression, irregular periods, hypotonic bladder based on sensory decrease of the bladder or hypotonic bladder accompanied by sensory paralysis of the bladder after surgery of the pelvic viscera, or constipation (preferably constipation), or the like.

Where the compound or its salt, which is obtained by the screening methods of the present invention, is used as a pharmaceutical composition, the compound or its salt can be formed into a pharmaceutical preparation in a conventional manner.

For example, the compound can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate80™ and HCO-50), etc. As an oily medium, for example, sesame oil, soybean oil or the like may be used, which can be used in combination with a dissolution aid such as benzyl benzoate, benzyl alcohol, etc.

Furthermore, the pharmaceutical drug described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salt varies depending on subject to be administered, target organ, conditions, methods for administration, etc.; in oral administration, the compound or its salt that decreases the expression level of the GPR39 is administered to the patient with, e.g., irritable bowel syndrome (as 60 kg body weight) normally in a daily dose of about 0.1 mg to about 100 mg, preferably about 1.0 to about 50 mg, and more preferably about 1.0 to about 20 mg per day. In parenteral administration, its single dose varies depending on subject to be administered, target organ, conditions, method for administration, etc., but generally in the form of injectable preparation, the compound or its salt that decreases the expression level of the GPR39 is advantageously administered intravenously to the patient with, e.g., irritable bowel syndrome in a daily dose of about 0.01 to about 30 mg, preferably about 0.1 to about 20 mg, and more preferably about 0.1 to about 10 mg. For other animal species, the corresponding dose as converted per 60 kg body weight can be administered.

(4) Method of Diagnosis Using the Antibody of the Present Invention

The antibodies of the present invention are capable of specifically recognizing the GPR39. Therefore, the antibodies can be used to detect or neutralize the GPR39 in a test fluid.

That is, the present invention provides, for example, the following quantification methods:

(i) a method for quantification of the GPR39 in a test fluid, which comprises competitively reacting the antibody of the present invention with the test fluid and a labeled form of the GPR39, and measuring a ratio of the labeled GPR39 bound to the antibody; and, (ii) a method for quantification of the GPR39 in a test fluid, which comprises reacting the test fluid with the antibody of the present invention immobilized on a carrier and a labeled form of the antibody of the present invention simultaneously or sequentially, and measuring the activity of the label on the immobilized carrier.

In the quantification method (ii) described above, it is preferred that one antibody recognizes the N-terminal region of the GPR39, and another antibody reacts with the C-terminal region of the GPR39.

Using the monoclonal antibodies to the GPR39, the GPR39 can be assayed. The GPR39 can also be detected by tissue staining or the like. For this purpose, the antibody molecule itself may be used, or $F(ab')_2$, Fab' or Fab fractions of the antibody molecule may also be used.

The quantification methods of the GPR39 using the antibodies of the present invention are not particularly limited. Any quantification method can be used, so long as the amount of antibody, antigen, or antibody-antigen complex corresponding to the amount of antigen (e.g., the amount of the GPR39) in the test fluid can be detected by chemical or physical means and the amount of the antigen can be calculated from a standard curve prepared from standard solutions containing known amounts of the antigen. For example, nephrometry, competitive methods, immunometric method, and sandwich method are appropriately used, with the sandwich method described below being most preferable in terms of sensitivity and specificity.

As the labeling agent for the methods using labeled substances, there are employed, for example, radioisotopes, enzymes, fluorescent substances, luminescent substances, etc. For the radioisotope, for example, $[^{125}I]$, $[^{131}I]$, $[^{3}H]$, $[^{14}C]$ and the like are used. As the enzyme described above, stable enzymes with high specific activity are preferred; for example, β-galactosidase, β-glucosidase, alkaline phosphatase, peroxidase, malate dehydrogenase and the like are used. Examples of the fluorescent substance used are fluorescamine and fluorescein isothiocyanate are used. For the luminescent substance, there are used, for example, luminol, luminol derivatives, luciferin, and lucigenin. Furthermore, the biotin-avidin system may be used for binding antibody or antigen to the label.

For immobilization of antigen or antibody, physical adsorption may be used. Chemical binding methods conventionally used for insolubilization or immobilization of the GPR39, enzymes or the like may also be used. For the carrier, for example, insoluble polysaccharides such as agarose, dextran, cellulose, etc.; synthetic resin such as polystyrene, polyacrylamide, silicon, etc., and glass or the like are used.

In the sandwich method, the immobilized monoclonal antibody of the present invention is reacted with a test fluid (primary reaction), then with the labeled monoclonal antibody of the present invention (secondary reaction), and the activity of the label on the immobilizing carrier is measured, whereby the amount of the GPR39 in the test fluid can be quantified. The order of the primary and secondary reactions may be reversed, and the reactions may be performed simultaneously or with an interval. The methods of labeling and immobilization can be performed by the methods described above. In the immunoassay by the sandwich method, the antibody used for immobilized or labeled antibodies is not necessarily one species, but a mixture of two or more species of antibody may be used to increase the measurement sensitivity.

In the methods of assaying the GPR39 by the sandwich method present invention, antibodies that bind to different sites of the GPR39 are preferably used as the monoclonal antibodies of the present invention for the primary and secondary reactions. That is, in the antibodies used for the primary and secondary reactions are, for example, when the antibody used in the secondary reaction recognizes the C-terminal region of the GPR39, it is preferable to use the antibody recognizing the region other than the C-terminal region for the primary reaction, e.g., the antibody recognizing the N-terminal region.

The monoclonal antibodies of the present invention can be used for the assay systems other than the sandwich method, for example, competitive method, immunometric method, nephrometry, etc.

In the competitive method, antigen in a test fluid and the labeled antigen are competitively reacted with antibody, and the unreacted labeled antigen (F) and the labeled antigen bound to the antibody (B) are separated (B/F separation). The amount of the label in B or F is measured, and the amount of the antigen in the test fluid is quantified. This reaction method includes a liquid phase method using a soluble antibody as an antibody, polyethylene glycol for B/F separation and a secondary antibody to the soluble antibody, and an immobilized method either using an immobilized antibody as the primary antibody, or using a soluble antibody as the primary antibody and immobilized antibody as the secondary antibody.

In the immunometric method, antigen in a test fluid and immobilized antigen are competitively reacted with a definite amount of labeled antibody, the immobilized phase is separated from the liquid phase, or antigen in a test fluid and an excess amount of labeled antibody are reacted, immobilized antigen is then added to bind the unreacted labeled antibody to the immobilized phase, and the immobilized phase is separated from the liquid phase. Then, the amount of the label in either phase is measured to quantify the antigen in the test fluid.

In the nephrometry, insoluble precipitate produced after the antigen-antibody reaction in gel or solution is quantified. When the amount of antigen in the test fluid is small and only a small amount of precipitate is obtained, laser nephrometry using scattering of laser is advantageously employed.

For applying these immunological methods to the measurement methods of the present invention, any particular conditions or procedures are not required. Systems for measuring the GPR39 are constructed by adding the usual technical consideration in the art to the conventional conditions and procedures. For the details of these general technical means, reference can be made to the following reviews and texts.

For example, Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing).

As described above, the GPR39 can be quantified with high sensitivity, using the antibodies of the present invention.

Where a decreased level of the GPR39 is detected by quantifying the GPR39 level using the antibodies of the present invention, it can be diagnosed that one suffers from, for example, diseases associated with dysfunction of the GPR39, or it is highly likely to suffer from these disease in the future.

Where an increased level of the GPR39 is detected, it can be diagnosed that one suffers from, for example, diseases caused by hyperfunction of the GPR39, or it is highly likely to suffer from these disease in the future.

The diseases associated with hyperfunction of the GPR39 include (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or vomiting which might be induced by functional bowel disorders caused by gastrointestinal motility disturbances, irritable bowel syndrome, fecal incontinence, colitis or Crohn's disease; or the like.

(5) Method of Screening Agonists to the GPR39

The cholesterol metabolism-related substance binds to the GPR39 so that an increase of the intracellular $Ca^{2+}$ level is observed. Thus, the GPR39 is useful as a reagent for searching or determining agonists (including naturally occurring ligands and synthetic ligands) to the GPR39 other than the cholesterol metabolism-related substance, using this intracellular signal as an indicator.

That is, the present invention provides a method of determining the agonist to the GPR39, which comprises assaying the GPR39-mediated intracellular $Ca^{2+}$ level increasing activity, when a test compound or its salt is brought in contact with a cell containing the GPR39.

Examples of test compounds include publicly known ligands (for example, angiotensin, bombesin, canavinoid, cholecystokinin, glutamine, serotonin, melatonin, neuropeptide Y, opioids, purines, vasopressin, oxytocin, PACAP (e.g., PACAP27, PACAP38), secretin, glucagon, calcitonin, adrenomedulin, somatostatin, GHRH, CRF, ACTH, GRP, PTH, VIP (vasoactive intestinal and related polypeptide), somatostatin, dopamine, motilin, amylin, bradykinin, CGRP (calcitonin gene-related peptide), leukotrienes, pancreastatin, prostaglandins, thromboxane, adenosine, adrenaline, the chemokine superfamily (e.g., the CXC chemokine subfamily such as IL-8, GROα, GROβ, GROγ, NAP-2, ENA-78, GCP-2, PF4, IP-10, Mig, PBSF/SDF-1, etc.; the CC chemokine subfamily such as MCAF/MCP-1, MCP-2, MCP-3, MCP-4, eotaxin, RANTES, MIP-1α, MIP-1β, HCC-1, MIP-3α/LARC, MIP-3β/ELC, I-309, TARC, MIPF-1, MIPF-2/eotaxin-2, MDC, DC-CK1/PARC, SLC, etc.; the C chemokine subfamily such as lymphotactin, etc.; the CX3C chemokine subfamily such as fractalkine, etc.), endothelin, enterogastrin, histamine, neurotensin, TRH, pancreatic polypeptide, galanin, lysophosphatidic acid (LPA), sphingosine 1-phosphate, etc.) as well as other substances, for example, tissue extracts, cell culture supernatants from humans or mammals (e.g., mice, rats, swine, bovine, sheep, monkeys, etc.) or low molecular synthetic compound. For example, the tissue extract, or cell culture supernatant, is added to the GPR39 while assaying the cell-stimulating activities and fractionating to finally obtain a single ligand.

The salts of the test compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

(6) Method of screening a compound or its salt that alters the binding property of the GPR39 to the cholesterol metabolism-related substance, or a compound or its salt (agonist, antagonist, etc.) that modulates the signal transduction induced by the binding of the GPR39 to the cholesterol metabolism-related substance, and a medicament comprising a compound or its salt that alters the binding property of the GPR39 to the cholesterol metabolism-related substance, or a compound or its salt that modulates the signal transduction induced by the binding of the GPR39 to the cholesterol metabolism-related substance By using the GPR39, or by constructing a recombinant of the GPR39 expression system and using the receptor-binding assay system via the expression system, the compound (e.g., peptide, protein, a non-peptide compound, a synthetic compound, a fermentation product, etc.) or salts thereof that alter the binding properties of the cholesterol metabolism-related substance as a ligand for the GPR39, or the compound (e.g., peptide, protein, a non-peptide compound, a synthetic compound, a fermentation product, etc.) or salts thereof that modulate the signal transduction induced by the binding of the cholesterol metabolism-related substance to the GPR39 can be screened efficiently.

Examples of such a compound or its salts include (a) a compound or its salt showing the cell stimulating activities mediated by the GPR39 (a so-called agonist to the GPR39), (b) a compound or its salt having no such cell stimulating activities (a so-called antagonist to the GPR39), (c) a compound or its salt that potentiates the binding affinity of the cholesterol metabolism-related substance to the GPR39, or (d) a compound or its salt that decreases the binding affinity of the cholesterol metabolism-related substance to the GPR39, and the like.

That is, the present invention provides a method of screening a compound or its salt that alters the binding properties of the GPR39 to the cholesterol metabolism-related substance, or the compound or its salt or its salt that modulates the signal transduction induced by the binding of the cholesterol metabolism-related substance to the GPR39, which comprises comparing the following two cases: (i) the case wherein the GPR39 is brought in contact with the cholesterol metabolism-related substance; and (ii) the case wherein the GPR39 is brought in contact with the cholesterol metabolism-related substance and a test compound.

According to the screening method of the present invention, the method is characterized by assaying, e.g., the binding amounts of the cholesterol metabolism-related substance to the GPR39, the cell-stimulating activities, etc. in (i) and (ii) and comparing (i) and (ii).

Examples of the cell-stimulating activities include the activities that promote or suppress arachidonic acid release, acetylcholine release, intracellular $Ca^{2+}$ release (intracellular $Ca^{2+}$ level increasing), intracellular cAMP production, intracellular cGMP production, inositol phosphate production, changes in cell membrane potential, phosphorylation of intracellular proteins, activation of c-fos, pH reduction, etc. Among them, the intracellular $Ca^{2+}$ level increasing activity and the like are preferred.

More specifically, the present invention provides the following methods.

a) A method of screening a compound or its salt that alters the binding properties of the cholesterol metabolism-related substance to the GPR39, or the compound or its salt that modulates the signal transduction induced by the binding of the cholesterol metabolism-related substance to the GPR39, which comprises measuring the binding amounts of a labeled form of the cholesterol metabolism-related substance to the GPR39 a) in the case wherein the labeled cholesterol metabolism-related substance is brought in contact with the GPR39 and b) in the case wherein the labeled cholesterol metabolism-related substance and a test compound are brought in contact with the GPR39, and comparing the cases.

b) A method of screening a compound or its salt that alters the binding properties of the cholesterol metabolism-related substance to the GPR39, or the compound or its salt that modulates the signal transduction induced by the binding of the cholesterol metabolism-related substance to the GPR39, which comprises measuring the binding amount of labeled cholesterol metabolism-related substance to a cell containing the GPR39 or a membrane fraction of the cell, in the case wherein the labeled cholesterol metabolism-related substance is brought in contact with the cell containing the GPR39 or the membrane fraction and in the case wherein the labeled cholesterol metabolism-related substance and a test compound are brought in contact with the cell containing the GPR39 or its membrane fraction, and comparing the cases.

c) A method of screening a compound or its salt that alters the binding properties of the cholesterol metabolism-related substance to the GPR39, or the compound or its salt that modulates the signal transduction induced by the binding of the cholesterol metabolism-related substance to the GPR39, which comprises measuring the amount of a labeled form of the cholesterol metabolism-related substance bound to the GPR39, in the case wherein the labeled cholesterol metabolism-related substance is brought in contact with the GPR39 expressed on a cell membrane by culturing a transformant containing the DNA of the present invention and in the case wherein the labeled cholesterol metabolism-related substance and a test compound are brought in contact with the GPR39 expressed in the cell membrane by culturing a transformant containing the DNA of the present invention, and comparing the cases.

d) A method of screening a compound or its salt that alters the binding properties of the cholesterol metabolism-related substance to the GPR39, or the compound or its salt that modulates the signal transduction induced by the binding of the cholesterol metabolism-related substance to the GPR39, which comprises assaying the cell stimulating activities mediated by the GPR39 in the case wherein a compound (e.g., cholesterol metabolism-related substance, etc.) that activates the GPR39 is brought in contact with a cell containing the GPR39 and in the case wherein said compound that activates the GPR39 and a test compound are brought in contact with the cell containing the GPR39, and comparing the cell stimulating activities between the two cases.

e) A method of screening a compound or its salt that alters the binding properties of the cholesterol metabolism-related substance to the GPR39, or the compound or its salt that modulates the signal transduction induced by the binding of the cholesterol metabolism-related substance to the GPR39, which comprises assaying the receptor protein-mediated cell stimulating activities in the case wherein a compound (e.g., the cholesterol metabolism-related substance, etc.) that activates the GPR39 is brought in contact with the GPR39 expressed on a cell membrane by culturing a transformant containing the DNA of the present invention and in the case wherein said compound that activates the GPR39 and a test compound are brought in contact with the GPR39 expressed on a cell membrane by culturing a transformant containing the DNA of the present invention, and comparing the cell stimulating activities between the two cases.

Further as the ligand for the GPR39, a compound or its salt that alters the binding properties of the cholesterol metabolism-related substance to the GPR39 (a synthetic low molecular compound, especially a synthetic low molecular agonist) can also be used, in place of the cholesterol metabolism-related substance described above. The compound or its salt that alters the binding properties of the cholesterol metabolism-related substance to the GPR39 can be obtained by carrying out the screening methods of the present invention later described, using as the ligand, e.g., the cholesterol metabolism-related substance. In the following screening methods, the compounds including the compound or its salt that alters the binding properties of the cholesterol metabolism-related substance to the GPR39 are briefly referred to as the ligand.

Hereinafter the screening method of the present invention will be described more specifically.

First, the GPR39, which is used for the screening method of the present invention, may be any one so long as it contains the GPR39 described above, though membrane fractions from mammalian organs are preferably employed. Since it is very difficult to obtain human-derived organs especially, human-derived GPR39, etc. expressed abundantly by use of recombinants are suitable for use in the screening.

In manufacturing the GPR39, the methods described above can be used, and the DNA of the present invention is preferably expressed on mammalian cells or insect cells. As the DNA fragment encoding the target protein region, a complementary DNA may be used but is not limited thereto. For example, gene fragments or a synthetic DNA may also be used. In order to introduce the DNA fragment encoding the GPR39 into host animal cells and express the same efficiently, the DNA fragment is preferably incorporated into a polyhedron promoter of nuclear polyhedrosis virus (NPV) belonging to the Baculovirus, an SV40-derived promoter, a promoter of retrovirus, a metallothionein promoter, a human heat shock promoter, a cytomegalovirus promoter, SRα promoter, etc. at the downstream thereof The quantity and quality of the thus expressed receptors can be examined by a publicly known method, for example, by the method described in the literature [Nambi, P. et al., J. Biol. Chem., 267, 19555-19559, 1992].

Accordingly, in the screening method of the present invention, the substance containing the GPR39 may be the GPR39 purified by publicly known methods, or a cell containing the said the GPR39 or a membrane fraction of the cell containing the GPR39 may be used as well.

Where the cell containing the GPR39 is used in the screening method of the present invention, the cell may be fixed with glutaraldehyde, formalin, etc. The fixation may be carried out by a publicly known method.

The cell containing the GPR39 refers to a host cell expressing the GPR39. Examples of such a host cell include *Escherichia coli, Bacillus subtilis*, yeast, insect cells, animal cells, etc.

The membrane fraction of the cell containing the GPR39 means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the GPR39 expressed and membrane components such as cell-derived phospholipids, membrane proteins, etc.

The amount of the GPR39 in a cell containing the GPR39 or the cell membrane fraction is preferably $10^3$ to $10^8$ molecules per cell, more preferably $10^5$ to $10^7$ molecules per cell. As the level of expression increases, the ligand binding activity per unit of membrane fraction (specific activity) increases so that not only the highly sensitive screening system can be constructed but also large quantities of samples can be assayed with the same lot.

To perform a) through c) above for screening the compound or its salt that alters the binding properties of the ligand to the GPR39, or the compound or its salt that modulates the signal transduction induced by the binding of the ligand to the GPR39, an appropriate fraction of the GPR39 and labeled ligand are required.

The GPR39 fraction is preferably a fraction of the GPR39 of naturally occurring type or fraction of the GPR39 of recombinant type having an activity equivalent thereto. Herein, the equivalent activity is intended to mean the ligand binding activity or the signal transduction activity.

As labeled cholesterol metabolism-related substances, a labeled cholesterol metabolism-related substance, a labeled cholesterol metabolism-related substance analogue and the like are employed. For example, there are used cholesterol metabolism-related substances labeled with $[^3H]$, $[^{125}I]$, $[^{14}C]$ $[^{35}S]$, etc.

Specifically, the compound or its salt that alters the binding properties of the ligand to the GPR39, the compound or its salt that modulates the signal transduction induced by the binding of the ligand to the GPR39 is screened by the following procedures. First, a preparation of the GPR39 is prepared by suspending a cell containing the GPR39 or a membrane fraction of the cell in a buffer appropriate for use in the screening method. Any buffer can be used so long as it does not interfere the binding affinity of the ligand to the GPR39, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor protein or ligand by a protease, a protease inhibitor such as PMSF, leupeptin, E-64 (manufactured by Peptide Institute, Inc.), pepstatin, etc. may also be added. A given amount (5,000 cpm to 500,000 cpm) of a labeled form of the ligand is added to 0.01 ml to 10 ml of the receptor protein solution, in which $10^{-4}$ M to $10^{-10}$ M of a test compound is co-present. To determine the amount of non-specific binding (NSB), a reaction tube containing an unlabeled form of the compound or its salt that alters the binding properties of the ligand to the GPR39 in a large excess is also provided. The reaction is carried out at approximately 0° C. to 50° C., preferably approximately 4° C. to 37° C. for about 20 minutes to about 24 hours, preferably about 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$ minus NSB) is made 100%, the test compound showing the specific binding amount (B minus NSB) of, e.g., 50% or less may be selected as a candidate compound.

The method d) or e) described above for screening the compound or its salt that alters the binding properties of the ligand to the GPR39, or the compound or its salt that modulates the signal transduction induced by the binding of the ligand to the GPR39 can be performed as follows. For example, the cell-stimulating activities mediated by the GPR39 can be determined by a publicly known method, or using an assay kit commercially available.

Specifically, the cells containing the GPR39 are first cultured in a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., cAMP, arachidonic acid, etc.) due to a degrading enzyme contained in the cells, an inhibitor against such as a degrading enzyme may be added prior to the assay. For detecting the activities such as the cAMP production suppression activity, the baseline production in the cells is increased by forskolin or the like and the suppressing effect on the increased baseline production can be detected.

For screening through the assay for the cell stimulating activities, cells, in which an appropriate type of the GPR39 has been expressed, are necessary. Preferred cells, in which the GPR39 has been expressed, are a cell line containing the GPR39 of naturally occurring type and the aforesaid cell line, in which the GPR39 of recombinant type has been expressed.

Examples of the test compounds include peptides, proteins, non-peptide compounds, synthetic compounds, fermentation products, cell extracts, plant extracts, animal tissue extracts, etc. These test compounds may be either novel or publicly known compounds.

The salts of the test compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The test compound which is preferably used is a compound designed to bind to the ligand-binding pocket, based on the atomic coordinate and the position of the ligand-binding pocket in the active site of the GPR39. The atomic coordinate and the position of the ligand-binding pocket in the active site of the GPR39 can be determined by publicly known methods or modifications thereof.

Following the method of screening the agonist to the GPR39 described above, it can be confirmed whether the compound that alters the binding properties of the ligand to the GPR39 is either an agonist or an antagonist.

A specific procedure to assess may involve (i) or (ii) below.
(i) Binding assay as given for the screening methods a) to c) described above is performed to obtain a compound that alters the binding properties (especially inhibits the binding) of the cholesterol metabolism-related substance to the GPR39. Then, it is determined whether or not the compound has the cell stimulating activities described above. The compound or its salt, which has the cell stimulating activities, is an agonist for the GPR39, whereas the compound or its salt having no such activities is an antagonist to the GPR39.
(ii) (a) A test compound is brought in contact with a cell containing the GPR39 and the cell stimulating activities described above are assayed. The compound or its salt having the cell stimulating activities is an agonist for the GPR39.
(b) The cell stimulating activities mediated by the GPR39 are assayed and compared between the case where the compound (e.g., the cholesterol metabolism-related substance) that activates the GPR39 is brought in contact with a cell containing the GPR39 and the case where the compound that activates the GPR39 and a test compound are brought in contact with a cell containing the GPR39 of the present invention. The compound or its salt that can decrease the cell stimulating activities by the compound activating the GPR39 is an antagonist to the GPR39.

The kit for screening the compound or its salt that alters the binding property of the ligand to the GPR39, or the compound or its salt that modulates the signal transduction induced by the binding of the ligand to the GPR39 comprises the GPR39, a cell containing the GPR39, or a membrane fraction of the cell containing the GPR39, etc.

Examples of the screening kit of the present invention include the following.

1. Reagent for Screening a) Assay Buffer and Wash Buffer

Hanks' balanced salt solution (manufactured by Gibco, Inc.) supplemented with 0.05% bovine serum albumin (manufactured by Sigma, Inc.)

The solution is sterilized by filtration through a 0.45 µm filter, and stored at 4° C. or may be prepared at use.

b) Preparation of the GPR39

CHO cells wherein the GPR39 has been expressed are passaged in a 12-well plate at a density of $5 \times 10^5$ cells/well followed by culturing at 37° C. under 5% $CO_2$ and 95% air for 2 days.

c) Labeled Cholesterol Metabolism-Related Substance

Commercially available cholesterol metabolism-related substances labeled with [$^3$H], [$^{125}$I], [$^{14}$C], [$^{35}$S], etc.

An aqueous solution of the substance is stored at 4° C. or −20° C., and diluted to 1 µM with the assay buffer upon use.

d) Standard Solution of the Cholesterol Metabolism-Related Substance

The cholesterol metabolism-related substance is dissolved in and adjusted to 1 mM with PBS containing 0.1% bovine serum albumin (manufactured by Sigma, Inc.) and stored at −20° C.

2. Assay Method a) CHO cells wherein the receptor protein of the present invention has been expressed are cultured in a 12-well culture plate and washed twice with 1 ml of the assay buffer, and 490 µl of the assay buffer is added to each well.

b) After adding 5 µl of $10^{-3}$-$10^{-10}$ M test compound solution, 5 µl of a labeled form of the cholesterol metabolism-related substance is added to the mixture, and the cells are incubated at room temperature for an hour. To determine the amount of the non-specific binding, 5 µl of the cholesterol metabolism-related substance is added in place of the test compound.

c) The reaction solution is removed, and the wells are washed 3 times with the washing buffer. The labeled ligand bound to the cells is dissolved in 0.2N NaOH-1% SDS, and mixed with 4 ml of liquid scintillator A (manufactured by Wako Pure Chemical Industries, Ltd.)

d) The radioactivity is measured using a liquid scintillation counter (manufactured by Beckman Co.), and the percent maximum binding (PMB) is calculated by the equation below.

$$PMB = [(B-NSB)/(B_0-NSB)] \times 100$$

PMB: Percent maximum binding
B: Value obtained in the presence of a test compound
NSB: Non-specific binding $B_0$: Maximum binding The compound or its salt, which is obtained by using the screening methods or the screening kits of the present invention, is the compound or its salt that alters the binding properties of the cholesterol metabolism-related substance to the GPR39, or the compound or its salt that modulates the signal transduction occurring by the binding of the cholesterol metabolism-related substance to the GPR39. Specifically, the compound is: (a) a compound or its salt having the cell-stimulating activities mediated by the GPR39 (a so-called agonist to the GPR39); (b) a compound or its salt having no cell stimulating activity (a so-called antagonist to the GPR39); (c) a compound or its salt that potentiates the binding affinity of the cholesterol metabolism-related substance to the GPR39; or (d) a compound or its salt that reduces the binding affinity of the cholesterol metabolism-related substance to the GPR39.

The compound obtained by using the screening method or the screening kit of the present invention may be peptides, proteins, non-peptide compounds, synthetic compounds, fermentation products, and may be novel or known compounds.

The salts of the compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Since the agonists for the GPR39 have the same physiological activities as the cholesterol metabolism-related substance, which is a ligand for the GPR39, the agonists are useful as safe and low toxic pharmaceuticals, correspondingly to the physiological activities possessed by the cholesterol metabolism-related substance.

Since the antagonists to the GPR39 can suppress the physiological activities possessed by the cholesterol metabolism-related substance, which is a ligand for the GPR39, the antagonists are useful as safe and low toxic pharmaceuticals to suppress the physiological activities of the cholesterol metabolism-related substance.

The compound or its salt that potentiates the binding affinity of the cholesterol metabolism-related substance to the GPR39 can potentiate the physiological activities possessed by the cholesterol metabolism-related substance, and is thus useful as a safe and low toxic medicament correspondingly to the physiological activities possessed by the cholesterol metabolism-related substance.

The compound or its salt that decreases the binding affinity of cholesterol metabolism-related substance to the GPR39 can decrease the physiological activities possessed by the cholesterol metabolism-related substance, and is thus useful as a safe and low toxic medicament to suppress the physiological activities of the cholesterol metabolism-related substance.

Specifically, the antagonist to the GPR39 or the compound or its salt that potentiates the binding affinity of the cholesterol metabolism-related substance to the GPR39 is useful as an agent for preventing/treating, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like.

Furthermore, the agonist for the GPR39, the cholesterol metabolism-related substance or the compound or its salt that potentiates the binding affinity of the cholesterol metabolism-related substance to the GPR39 is useful as an agent for preventing/treating, for example, growth retardation, lacerations, burn injury, poor circulation, decline in learning ability, hypogonadism, dysgeusia, anosmia, hyperplasia, arteriosclerosis, myocardial infarction, apoplexy, hepatic cirrhosis, cholesterol accumulation, reduced resistance to infections, gout, cancer, hard labor, mellitus diabetes, blemish, anemia, depilation, respiratory disorders, indigestion, cardiopathy, gray hair, swelling, wrinkle, skin sagging, hypothyroidism, depression, irregular periods, hypotonic bladder based on sensory decrease of the bladder or hypotonic bladder accompanied by sensory paralysis of the bladder after surgery of the pelvic viscera, or constipation (preferably constipation), or the like. Furthermore, there are useful as an agent for promoting the secretion of cytokines (e.g., IL-8), etc.

Where the compound or its salt obtained by using the screening methods or the screening kit of the present invention is used as a pharmaceutical composition, the compound or its salt can be prepared into a pharmaceutical preparation in a conventional manner.

For example, the compound or its salt can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate80™ and HCO-50), etc. As an oily medium, for example, sesame oil, soybean oil or the like may be used, and may be used in combination with a dissolution aid such as benzyl benzoate, benzyl alcohol, etc.

Furthermore, the drugs described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salt may vary depending on subject to be administered, target organ, conditions, route for administration, etc.; in oral administration, the antagonist to the GPR39 is administered to the patient with, e.g., irritable bowel syndrome (as 60 kg body weight) normally in a daily dose of about 0.1 mg to about 100 mg, preferably about 1.0 to about 50 mg, and more preferably about 1.0 to about 20 mg per day. In parenteral administration, its single dose varies depending on subject to be administered, target organ, conditions, method for administration, etc., but generally in the form of injectable preparation, the antagonist to the GPR39 is advantageously administered intravenously to the patient with, e.g., irritable bowel syndrome in a daily dose of about 0.01 to about 30 mg, preferably about 0.1 to about 20 mg, and more preferably about 0.1 to about 10 mg. For other animal species, the corresponding dose as converted per 60 kg body weight can be administered.

(7) Methods for Elucidation of the Action Mechanism of Various Drugs

By using the GPR39, it can be confirmed whether or not various drugs exhibit their pharmacological effects mediated by the GPR39.

That is, the present invention provides the following methods.

(1) A method of confirmation that the agent for preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like, binds to the GPR39, which comprises using the GPR39.

(2) A method of confirmation that the agent for preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like, is an antagonist to the GPR39, which comprises using the GPR39.

(3) The screening method according to (1) to (2) described above, wherein the binding amount of each drug to the GPR39 is determined when the drug is brought in contact with the GPR39.

The confirmation methods can be performed by using the drug described above in lieu of the test compound in the aforesaid methods of screening the compound that alters the binding properties of the cholesterol metabolism-related substance to the GPR39.

The kit used for the confirmation methods of the present invention comprises the drug described above in place of the test compound, in the aforesaid kit for screening the compound that alters the binding properties of the cholesterol metabolism-related substance to the GPR39.

By using the confirmation methods of the present invention as such, it can be confirmed that various drugs commercially available or under development exhibit their pharmacological effects mediated by the GPR39.

(8) Medicament Comprising the Compound or its Salt that Changes the Amount of the GPR39 or its Partial Peptide in Cell Membrane The antibody of the present invention is capable of specifically recognizing the GPR39 and can be used for screening the compound or its salt that changes the amount of the GPR39 in cell membrane.

That is, the present invention provides the following methods:

(i) a method of screening the compound or its salt that changes the amount of the GPR39 in the cell membrane, which comprises measuring the amount of the GPR39 contained in a) blood, b) particular organs or c) a cell membrane fraction isolated after disrupting tissues or cells isolated from the organs of non-human mammals;

(ii) a method of screening the compound or its salt that changes the amount of the GPR39 in the cell membrane, which comprises disrupting transformants, etc. expressing the GPR39, isolating the cell membrane fraction and quantifying the GPR39 contained in the cell membrane fraction; and, (iii) a method of screening the compound or its salt that changes the amount of the GPR39 in the cell membrane, which comprises preparing a slice of a) blood, b) particular organs or c) tissues, cells, etc. isolated from organs of non-human mammals and quantifying the stained receptor protein in the cell surface using immunostaining assay thereby to confirm the protein in the cell membrane.

(iv) a method of screening the compound or its salt that changes the amount of the GPR39 in the cell membrane, which comprises preparing a slice of a transformant expressing the GPR39 and quantifying the stained receptor protein on the cell surface using immunostaining assay thereby to confirm the protein in the cell membrane.

Specifically, the GPR39 contained in the cell membrane fraction can be measured as follows.

(i) Normal or disease models of non-human mammals (e.g., mice, rats, rabbits, sheep, swine, bovine, cats, dogs, monkeys, more specifically, immunodeficiency models of rats, mice, rabbits, etc.) receive administration of a drug (e.g., an immunomodulator, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time. The mRNA of the TGR25 of the present invention contained in the thus obtained cells is extracted from the cells, for example, in a conventional manner and quantified by means of, e.g., TaqMan PCR, or may also be analyzed by northern blot technique by publicly known methods. The obtained organs, tissues, cells or the like are suspended in, for example, an appropriate buffer (e.g., Tris hydrochloride buffer, phosphate buffer, HEPES buffer, etc.), and the organs, tissues or cells are disrupted, and the cell membrane fraction is obtained using surfactants (e.g., Triton-X 100™, Tween 20™) and further using techniques such as centrifugal separation, filtration, column fractionation, etc.

The membrane fraction of the cell containing the GPR39 means a fraction abundant in cell membrane obtained by cell disruption and subsequent fractionation by publicly known methods. Cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, or the like. Cell membrane fractionation is effected mainly by fractionation using a centrifugal force, such as centrifugation for fractionation and density gradient centrifugation. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the GPR39 expressed and membrane components such as cell-derived phospholipids, membrane proteins, etc.

The GPR39 contained in the cell membrane fraction can be quantified by, for example, the sandwich immunoassay, western blot analysis, etc. using the antibody of the present invention.

The sandwich immunoassay can be performed as described above, and the western blot can be performed by publicly known methods.

(ii) Transformants expressing the GPR39 are prepared by the method described above, and the GPR39 contained in the cell membrane fraction can be quantified.

The compound or its salt that changes the amount of the GPR39 in cell membranes can be screened as follows.

(i) Normal non-human mammals or disease models of non-human mammals are administered with a test compound at a specified period of time before (30 minutes to 24 hours before, preferably 30 minutes to 12 hours before, more preferably 1 hour to 6 hours before), at a specified time after (30 minutes to 3 days after, preferably 1 hour to 2 days after, more preferably 1 hour to 24 hours after), or simultaneously with a drug or physical stress. At a specified time (30 minute to 3 days, preferably 1 hour to 2 days, more preferably 1 hour to 24 hours) after administration of the test compound, the amount of the GPR39 in the cell membranes can be quantified.

(ii) Transformants are cultured in a conventional manner and a test compound is mixed in the culture medium. After a specified time (after 1 day to 7 days, preferably after 1 day to 3 days, more preferably after 2 to 3 days), the amount of the GPR39 in the cell membranes can be quantified.

Specifically, the GPR39 contained in cell membrane fractions is confirmed as follows.

(iii) Normal non-human mammals or disease models of non-human mammals (e.g., mice, rats, rabbits, sheep, swine, bovine, cats, dogs, monkeys, more specifically, immunodeficiency models of rats, mice, rabbits, etc.) receive administration of a drug (e.g., an immunomodulator, etc.) or physical stress (e.g., soaking stress, electric shock, light and darkness, low temperature, etc.), and the blood, particular organs (e.g., brain, liver, kidney, etc.), or tissues or cells isolated from the organs are obtained after a specified period of time. Tissue sections are prepared from the thus obtained organs, tissues, cells, etc. in a conventional manner followed by immunostaining with the antibody of the present invention. The staining intensity of the receptor protein on the cell surface is quantified to confirm the protein on the cell membrane, whereby the amount of the GPR39 in the cell membrane can be confirmed quantitatively or qualitatively.

(iv) The confirmation can also be made by the similar method, using transformants expressing the GPR39.

The test compounds used may be peptides, proteins, non-peptide compounds, synthetic compounds, fermentation products, cell extracts, plant extract, animal tissue extracts, blood plasma, etc. These compounds may be novel or publicly known compounds.

The test compound may form salts, and these salts include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compounds or salts thereof obtained by using the screening methods of the present invention are compounds or salts thereof, which have the action of changing the amount of the GPR39 in cell membranes. Specifically, these compounds or salts thereof. are: (a) compounds or salts thereof that increase the amount of the GPR39 in cell membranes thereby to potentiate the cell stimulating activities mediated by the G protein-coupled receptor and (b) compounds or salts thereof that decrease the amount of the GPR39 in the cell membranes thereby to attenuate the cell stimulating activities.

The compounds may be peptides, proteins, non-peptide compounds, synthetic compounds, fermentation products, etc. These compounds may be novel or publicly known compounds.

The salts of the compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compound or its salt that increases the amount of the GPR39 in cell membranes thereby to potentiate the cell-stimulating activities is useful as a safe and low-toxic agent for the prevention/treatment of diseases associated with dysfunction of the GPR39.

The compound or its salt that decreases the amount of the GPR39 in cell membranes thereby to attenuate the cell-stimulating activities is useful as a safe and low-toxic agent for the prevention/treatment of diseases caused by overexpression of the GPR39.

Specifically, the compound or its salt that decreases the amount of the GPR39 in cell membranes is useful as an agent for the prevention/treatment of, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc.; or as an antiemetic agent for vomiting which might be induced by functional bowel disorders caused by gastrointestinal motility disturbances, irritable bowel syndrome, fecal incontinence, colitis or Crohn's disease; or the like.

Where the compound or its salt, which is obtained by using the screening methods of the present invention, is used as a pharmaceutical composition, the compound or its salt can be prepared into a pharmaceutical preparation in a conventional manner.

For example, the compound or its salt can be used orally in the form of tablets which may be tablets, if necessary, coated with sugar, capsules, elixirs, microcapsules, etc., or parenterally in the form of injectable preparations such as a sterile solution or a suspension in water or with other pharmaceutically acceptable liquid. These preparations can be manufactured, e.g., by mixing the compound or its salt, with a physiologically acceptable known carrier, flavoring agent, excipient, vehicle, antiseptic, stabilizer, binder, etc., in a unit dosage form required in a generally accepted manner applied to making pharmaceutical preparations. The active ingredient in the preparation is controlled in such an amount that an appropriate dose is obtained within the specified range given.

Additives miscible with tablets, capsules, etc. include a binder such as gelatin, corn starch, tragacanth or gum arabic, an excipient such as crystalline cellulose, a swelling agent such as corn starch, gelatin, alginic acid, etc., a lubricant such as magnesium stearate, a sweetening agent such as sucrose, lactose or saccharin, a flavoring agent such as peppermint, akamono oil or cherry, and the like. When the unit dosage is in the form of capsules, liquid carriers such as oils and fats may further be used together with the additives described above. A sterile composition for injection may be formulated following a conventional manner used to make pharmaceutical compositions, e.g., by dissolving or suspending the active ingredients in a vehicle such as water for injection with a naturally occurring vegetable oil such as sesame oil, coconut oil, etc. to prepare the pharmaceutical composition. Examples of an aqueous medium for injection include physiological saline, an isotonic solution containing glucose and other auxiliary agents (e.g., D-sorbitol, D-mannitol, sodium chloride, etc.) or the like, which may be used in combination with an appropriate dissolution aid such as an alcohol (e.g., ethanol), a polyalcohol (e.g., propylene glycol, polyethylene glycol), a nonionic surfactant (e.g., polysorbate 80™ and HCO-50), etc. As an oily medium, for example, sesame oil, soybean oil or the like may be used, which can be used in combination with a dissolution aid such as benzyl benzoate, benzyl alcohol, etc.

Furthermore, the preventive/therapeutic drug described above may also be formulated with a buffer (e.g., phosphate buffer, sodium acetate buffer), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the thus obtained pharmaceutical preparation is safe and low toxic, the preparation can be administered to human or mammals (e.g., rats, mice, rabbits, sheep, swine, bovine, cats, dogs, monkeys, etc.).

The dose of the compound or its salt may vary depending on subject to be administered, target organ, conditions, methods for administration, etc.; in oral administration, the compound or its salt that decreases the amount of the GPR39 in cell membranes is administered to the patient with, e.g., irritable bowel syndrome (as 60 kg body weight) normally in a daily dose of about 0.1 mg to about 100 mg, preferably about 1.0 to about 50 mg, and more preferably about 1.0 to about 20 mg per day. In parenteral administration, its single dose varies depending on subject to be administered, target organ, conditions, method for administration, etc;, but generally in the form of injectable preparation, the compound or its salt that decreases the amount of the GPR39 in cell membranes is advantageously administered intravenously to the patient with, e.g., irritable bowel syndrome in a daily dose of about 0.01 to about 30 mg, preferably about 0.1 to about 20 mg, and more preferably about 0.1 to about 10 mg. For other animal species, the corresponding dose as converted per 60 kg body weight can be administered.

(9) Medicament Comprising the Antibody to the GPR39

The neutralizing activity of the antibody to the GPR39 means the activity of inactivating the signal transduction function in which the GPR39 takes part. Thus, when the antibody has the neutralizing activity, the antibody can inactivate signal transduction in which the GPR39 takes part, for example, the GPR39-mediated cell stimulating activities (e.g., the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., especially, the intracellular $Ca^{2+}$ level increasing activity (intracellular $Ca^{2+}$ releasing activity)).

Therefore, the antibody (e.g., neutralizing antibody) to the GPR39 can be used as agents for preventing/treating diseases caused by hyperfunction, etc. of the GPR39, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like.

The preventive/therapeutic agents described above can be manufactured as in the medicaments comprising the GPR39 or the antagonists to the GPR39 described above and provided for use.

(10) Medicament Comprising the Antisense DNA of the Present Invention

The antisense DNA of the present invention can be used as agents for preventing/treating diseases caused by hyperfunction, etc. of the GPR39, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like.

For example, where the antisense DNA is used, the antisense DNA itself is administered; alternatively, the antisense DNA is inserted into an appropriate vector such as retrovirus vector, adenovirus vector, adenovirus-associated virus vector, etc. and then administered in a conventional manner. The antisense DNA may also be administered as naked, or with adjuvants to assist its uptake by gene gun or through a catheter such as a catheter with a hydrogel.

In addition, the antisense DNA may also be used as an oligonucleotide probe for diagnosis to investigate the presence of the DNA of the present invention or the state of its expression in tissues or cells.

(11) Preparation of Animal Bearing the DNA of the Present Invention

The present invention provides a non-human mammal bearing DNA which is exogenous (hereinafter briefly referred to as the exogenous DNA of the present invention) or its variant DNA (sometimes briefly referred to as the exogenous variant DNA of the present invention).

That is, the present invention provides:

[1] A non-human mammal bearing the exogenous DNA of the present invention or its variant DNA;

[2] The mammal according to [1], wherein the non-human mammal is a rodent;

[3] The mammal according to [2], wherein the rodent is mouse or rat; and,

[4] A recombinant vector containing the exogenous DNA of the present invention or its variant DNA and capable of expressing in a mammal; etc.

The non-human mammal bearing the exogenous DNA of the present invention or its variant DNA (hereinafter briefly referred to as the DNA transgenic animal of the present invention) can be produced by transferring a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, or the like by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57Bl/6 strain, DBA2 strain, etc. for a pure line and for a cross line, B6C3F$_1$, strain, BDF$_1$, strain B6D2F$_1$, strain, BALB/c strain, ICR strain, etc.), rats (Wistar, S D, etc.) or the like, since they are relatively short in ontogeny and life cycle from a standpoint of producing model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean DNA that expresses abnormal GPR39 and exemplified by the DNA that expresses GPR39, which suppresses the function of normal GPR39.

The exogenous DNA of the present invention may be any one of those derived from a mammal of the same species as, or a different species from, the mammal as the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the GPR39, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor $1\alpha$ (EF-$1\alpha$), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human protein elongation factor $1\alpha$ (EF-$1\alpha$) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for normal GPR39 can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal GPR39 obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof The offspring of the animal that inherits the exogenous DNA of the present invention also have the exogenous DNA of the present invention in all of the germinal cells and somatic cells thereof. The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the GPR39 by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the GPR39 and the pathological mechanism of the disease associated with the GPR39 and to investigate how to treat these diseases.

Furthermore, since a transgenic mammal with the exogenous normal DNA of the present invention exhibits an increasing symptom of the GPR39, the animal is usable for screening of a drug for the treatment of diseases associated with the GPR39.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the GPR39 by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the GPR39 and the pathological mechanism of the disease and to investigate how to treat the disease.

As a specific applicability, the transgenic animal expressing the abnormal DNA of the present invention at a high level is expected to serve as an experimental model to elucidate the mechanism of the functional inhibition (dominant negative effect) of the normal GPR39 by the abnormal GPR39 of the present invention in the function inactive type inadaptability to the GPR39.

Furthermore, a transgenic mammal with the exogenous normal DNA of the present invention exhibits an increasing symptom of the GPR39. Thus, the mammal is also expected to serve for screening a drug for the treatment of the function inactive type inadaptability to the GPR39.

Other potential applications of two kinds of the DNA transgenic animals of the present invention described above further include, for example:

(i) Use as a cell source for tissue culture;
(ii) Elucidation of the relation to the GPR39 that is specifically expressed or activated by the GPR39, by direct analysis of DNA or RNA in tissues of the DNA transgenic animal of the present invention or by analysis of the GPR39 tissues expressed by the DNA;
(iii) Research on the function of cells derived from tissues that are usually cultured only with difficulty, using cells in tissues bearing the DNA cultured by a standard tissue culture technique;
(iv) Screening a drug that enhances the functions of cells using the cells described in (iii) above; and,
(v) Isolation and purification of the variant GPR39 of the present invention and preparation of an antibody thereto.

Moreover, clinical conditions of a disease associated with the GPR39, including the function inactive type inadaptability to the GPR39 can be determined by using the DNA transgenic animal of the present invention. Also, pathological findings on each organ in a disease model associated with the GPR39 can be obtained in more detail, leading to the development of a new method for treatment as well as the research and therapy of any secondary diseases associated with the disease.

It is also possible to obtain a free DNA-transferred cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the GPR39, and to study in association with apoptosis, differentiation or propagation or on the mechanism of signal transduction in these properties to inspect any abnormality therein. Thus, the DNA transgenic animal can provide an effective research material for the GPR39 and for investigation of its function and effect.

To develop agents for the treatment of diseases associated with the GPR39, including the function inactive type inadaptability to the GPR39, using the DNA transgenic animal of the present invention, an effective and rapid method for screening can be provided by using the method for inspection and the method for quantification, etc. described above. It is also possible to investigate and develop a method for DNA therapy for the treatment of diseases associated with the GPR39, using the DNA transgenic animal of the present invention or a vector capable of expressing the exogenous DNA of the present invention.

(12) Knockout Animal

The present invention provides a non-human mammalian embryonic stem cell bearing the DNA of the present invention inactivated and a non-human mammal deficient in expressing the DNA of the present invention.

Thus, the present invention provides:

[1] A non-human mammalian embryonic stem cell in which the DNA of the present invention is inactivated;
[2] The embryonic stem cell according to [1], wherein the DNA is inactivated by introducing a reporter gene (e.g., β-galactosidase gene derived from *Escherichia coli*);
[3] The embryonic stem cell according to [1], which is resistant to neomycin;
[4] The embryonic stem cell according to [1], wherein the non-human mammal is a rodent;
[5] The embryonic stem cell according to [4], wherein the rodent is mouse;
[6] A non-human mammal deficient in expressing the DNA of the present invention, wherein the DNA is inactivated;
[7] The non-human mammal according to [6], wherein the DNA is inactivated by inserting a reporter gene (e.g., β-galactosidase derived from *Escherichia coli*) therein and the reporter gene is capable of being expressed under control of a promoter for the DNA of the present invention;
[8] The non-human mammal according to [6], which is a rodent;
[9] The non-human mammal according to [8], wherein the rodent is mouse; and,
[10] A method of screening a compound or its salt that promotes or inhibits (preferably inhibits) the promoter activity to the DNA of the present invention, which comprises administering a test compound to the mammal of [7] and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the GPR39 (hereinafter sometimes referred to as the knockout DNA of the present invention) by substantially inactivating the activities of the GPR39 encoded by the DNA (hereinafter merely referred to as ES cell).

As the non-human mammal, the same examples as described above apply

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon region thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter briefly referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the BDF$_1$ mouse (F$_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The BDF$_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In addition thereto, embryos, which are collected at the 8-cell stage and cultured until the blastocyte stage, are used to efficiently obtain a large number of early stage embryos.

Although the ES cells used may be of either sex, male ES cells are generally more convenient for generation of a germ cell line chimera. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for studying the GPR39 in vitro or the GPR39 cytologically.

The non-human mammal deficient in expression of the DNA of the present invention can be identified from a normal animal by measuring the mRNA level in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the GPR39. The individuals deficient in homozygous expression of the GPR39 can be obtained from offspring of the intercross between those deficient in heterozygous expression of the GPR39.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the GPR39, such an animal can be a disease model suspected of inactivated biological activities of the GPR39 and thus, offers an effective study to investigate the causes for and therapy for these diseases.

(12a) Method of Screening a Compound or its Salt having Therapeutic/Preventive Effects on Diseases Caused by Deficiency, Damages, Etc. of the DNA of the Present Invention The non-human mammal deficient in expression of the DNA of the present invention can be employed for screening of a compound or its salt having therapeutic/preventive effects on diseases caused by deficiency, damages, etc. of the DNA of the present invention.

That is, the present invention provides a method of screening a compound or its salt having a therapeutic/preventive effect on diseases caused by deficiency, damages, etc. of the DNA of the present invention, which comprises administering a test compound to a non-human mammal deficient in expression of the DNA of the present invention and, observing and measuring a change occurred in the animal.

As the non-human mammal deficient in expression of the DNA of the present invention, which can be employed for the screening method, the same examples as given hereinabove apply.

Examples of the test compound include peptides, proteins, non-peptide compounds, synthetic compounds, fermentation products, cell extracts, plant extracts, animal tissue extracts, blood plasma, etc. These compounds may be novel compounds or publicly known compounds.

The salts of the test compound used include salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/preventive effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately selected depending on the administration methods, nature of the test compound, etc.

When a test compound is administered to a test animal in the screening method and blood sugar level of the test animal increases by about 10% or more, preferably 30% or more, more preferably about 50% or more, the test compound can be selected to be a compound or its salt having a therapeutic/preventive effect on the diseases described above.

The compound obtained using the above screening method is a compound selected from the test compounds described above and can be used as a safe and low toxic drug such as a preventive/therapeutic drug. In addition, compounds derived from the compound obtained by the screening described above can be used as well.

As the salts of the compound obtained by the screening methods, there may be used salts with physiologically acceptable acids (e.g., inorganic acids, organic acids, etc.) or bases (e.g., alkali metals, etc.), particularly preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The medicament comprising the compound or its salt, which is obtained by the above screening methods, can be manufactured in a manner similar to the method for preparing the medicament comprising the compound or its salt that alters the binding properties of the GPR39 to the cholesterol metabolism-related substance, or the compound that modulates the signal transduction induced by the binding of the cholesterol metabolism-related substance to the GPR39, as described above.

Since the pharmaceutical preparation thus obtained is safe and low toxic, it can be administered to human or mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound or its salt is orally administered to the patient (as 60 kg body weight) with, e.g., diseases caused by deficiency, damages, etc. of the GPR39, the compound or its salt is generally administered to the patient with, e.g., diseases caused by deficiency, damages, etc. of the GPR39 in a daily dose of about 0.1 to about 100 mg, preferably about 1.0 to about 50 mg and, more preferably about 1.0 to about 20 mg. In parenteral administration, a single dose of said compound or its salt may vary depending upon target subject, target disease, etc. When the compound or its salt is administered to the patient (as 60 kg body weight) with, e.g., diseases caused by deficiency, damages, etc. of the GPR39 in the form of an injectable preparation, it is advantageous to administer the compound or its salt intravenously to the patient in a daily dose of about 0.01 to about 30 mg, preferably about 0.1 to about 20 mg, and more preferably about 0.1 to about 10 mg. For other animal species, the corresponding dose as converted per 60 kg body weight can be administered.

(12b) Method of Screening a Compound or its Salt that Promotes or Inhibits the Activity of a Promoter to the DNA of the Present Invention The present invention provides a method of screening a compound or its salts that promote or inhibit the activity of a promoter for the DNA of the present invention, which comprises administering a test compound to a non-human mammal deficient in expression of the DNA of the present invention and detecting the expression of the reporter gene.

In the screening method described above, an animal in which the DNA of the present invention is inactivated by introducing a reporter gene and the reporter gene is expressed under control of a promoter to the DNA of the present invention is used as the non-human mammal deficient in expression of the DNA of the present invention, which is selected from the aforesaid non-human mammals deficient in expression of the DNA of the present invention.

The same examples of the test compound apply to specific compounds used for the screening.

As the reporter gene, the same specific examples apply to this screening method. Preferably, there are used β-galactosidase (lacZ), soluble alkaline phosphatase gene, luciferase gene and the like.

Since the reporter gene is present under control of a promoter to the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the GPR39 is substituted with, e.g., β-galactosidase gene (lacZ) derived from *Escherichia coli*, β-galactosidase is expressed in a tissue where the GPR39 should originally be expressed, instead of the GPR39. Thus, the expression state of the GPR39 can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the GPR39, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compounds or their salts obtained using the screening methods described above are compounds or their salts that are selected from the test compounds described above and compounds or their salts that promote or inhibit the promoter activity to the DNA of the present invention.

As the salts of the compounds obtained by the screening methods, there may be used salts with physiologically acceptable acids (e.g., inorganic acids, etc.) or bases (e.g., organic acids, etc.), preferably physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

Since the compound or its salt that promotes the activity of a promoter for the DNA of the present invention can promote the expression of the GPR39 and can promote the function of the GPR39, the compound or its salt is useful as a medicament such as a preventive/therapeutic agent for diseases associated with dysfunction of the GPR39.

Since the compound or its salt that inhibits the activity of a promoter for the DNA of the present invention can inhibit the expression of the GPR39 and can inhibit the function of the GPR39, the compound or its salt is useful as a medicament such as a preventive/therapeutic agent for diseases associated with hyperfunction of the GPR39, or as an antiemetic agent for vomiting which might be induced by functional bowel disorders caused by gastrointestinal motility disturbances, irritable bowel syndrome, fecal incontinence, colitis or Crohn's disease.

The diseases associated with hyperfunction of the GPR39 include, for example, (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc.

In addition, compounds derived from the compounds obtained by the screening described above can be used as well.

The medicament comprising the compound or its salt obtained by the above screening method can be manufactured in a manner similar to the method for preparing the medicament comprising the compound or its salt that alters the binding properties of the GPR39 or its salt to the cholesterol metabolism-related substance.

Since the pharmaceutical preparation thus obtained is safe and low toxic, it can be administered to, for example, human or mammal (e.g., rat, mouse, guinea pig, rabbit, sheep, swine, bovine, horse, cat, dog, monkey, etc.).

The dose of the compound or its salt may vary depending upon target disease, subject to be administered, route of administration, etc. For example, when the compound or its salt that inhibits the activity of a promoter to the DNA of the present invention is orally administered to the patient (as 60 kg body weight) with, e.g., irritable bowel syndrome, the compound or its salt is generally administered in a daily dose of about 0.1 to about 100 mg, preferably about 1.0 to about 50 mg and, more preferably about 1.0 to about 20 mg. In parenteral administration, a single dose of said compound or its salt may vary depending upon target subject, target disease, etc. When the compound that inhibits the activity of a promoter to the DNA of the present invention is administered to the patient (as 60 kg body weight) with, e.g., irritable bowel syndrome in the form of an injectable preparation, it is advantageous to administer the compound or its salt intravenously to the patient in a daily dose of about 0.01 to about 30 mg, preferably about 0.1 to about 20 mg, and more preferably about 0.1 to about 10 mg. For other animal species, the corresponding dose as converted per 60 kg body weight can be administered.

As stated above, the non-human mammal deficient in expression of the DNA of the present invention is extremely useful for screening the compound or its salt that promotes or inhibits the promoter activities to the DNA of the present invention and can greatly contribute to elucidation of causes for various diseases suspected of deficiency in expression of the DNA of the present invention and for the development of preventive/therapeutic drug for these diseases.

Also, a so-called transgenic animal (gene transferred animal) can be prepared by using a DNA containing the promoter region of the GPR39, ligating genes encoding various proteins at the downstream and injecting the same into oocyte of an animal. It is thus possible to synthesize the GPR39 therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the GPR39 itself.

In the specification and drawings, the codes of bases, amino acids, etc. are shown by abbreviations and in that case, denoted in accordance with the IUPAC-IUB Commission on Biochemical Nomenclature or by the common codes in the art, examples of which are given below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |

-continued

| | |
|---|---|
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |
| * | corresponding to termination codon |
| Me | methyl group |
| Et | ethyl group |
| Bu | butyl group |
| Ph | phenyl group |
| TC | thiazolidine-4(R)-carboxamido group |

Substituents, protecting groups and reagents generally used in this specification are presented as the codes below.

| | |
|---|---|
| Tos | p-toluenesulfonyl |
| CHO | formyl |
| Bzl | benzyl |
| Cl$_2$-Bzl | 2,6-dichlorobenzyl |
| Bom | benzyloxymethyl |
| Z | benzyloxycarbonyl |
| Cl-Z | 2-chlorobenzyloxycarbonyl |
| Br-Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dicyclohexylcarbodiimide |

The sequence identification numbers in the sequence listing of the specification indicates the following sequence, respectively.

SEQ ID NO: 1

This shows the amino acid sequence of human-derived GPR39.

SEQ ID NO: 2

This shows the base sequence of cDNA encoding human-derived GPR39.

SEQ ID NO: 3

This shows the amino acid sequence of mouse-derived GPR39.

SEQ ID NO: 4

This shows the base sequence of cDNA encoding mouse-derived GPR39.

SEQ ID NO: 5

This shows the amino acid sequence of rat-derived GPR39.

SEQ ID NO: 6

This shows the base sequence of cDNA encoding rat-derived GPR39.

SEQ ID NO: 7

This shows the base sequence of a primer for TaqMan PCR used in EXAMPLE 4 below.

SEQ ID NO: 8

This shows the base sequence of a primer for TaqMan PCR used in EXAMPLE 4 below.

SEQ ID NO: 9

This shows the base sequence of a primer for TaqMan PCR used in EXAMPLE 4 below.

EXAMPLES

Hereinafter the present invention will be described in more detail by referring to EXAMPLES but is not deemed to limit the scope of the present invention thereto. The gene using *Escherichia coli* was performed according to the methods described in the Molecular Cloning.

Reference Example 1

Acquisition of Human GPR39, Rat GPR39 and Mouse GPR39-Expressing Cells cDNAs of human GPR39, rat GPR39 and mouse GPR39 were acquired from cDNA including the intestinal tract, respectively, based on known sequences of AF034633.1 (human), XM_222578 (rat), AK016817 and AK082941.1 (mouse). The DNA fragment obtained was inserted into the animal cell expression vector pAKKO-111H (the same pAKKO-1.11H as described in Biochem. Biophys. Acta, Hinuma, S. et al., 1219, 251-259, 1994). Using this vector, the GPR39-expressing CHO cells were acquired by a method per se publicly known.

Example 1

Transient Expression of G Protein-Coupled Receptor Protein Expression Plasmid and Reporter Plasmid in Host Cells (HeLa)

First, cDNA encoding G protein-coupled receptor protein, the GPR39 (SEQ ID NO: 1) prepared by the method publicly known was inserted into pAKKO-111H (the same plasmid vector as pAKKO-1.111H described in Biochem. Biophys. Acta, Hinuma, S. et al., 1219, 251-259, 1994). Using the expression plasmid for animal cells thus obtained, *Escherichia coli* JM109 was transfected and the colonies obtained were isolated and cultured. Thereafter, large scale plasmid preparation was carried out using QIAGEN Plasmid Maxi Kit (Qiagen). Furthermore, the pSRE-Luc reporter plasmid (Invitrogen) ligated with a luciferase gene as a reporter at the downstream of serum response element (SRE), and expression vector plasmids for human Gα0A, human Gβ1 and human Gγ2, which are a kind of G proteins, were prepared in a similar manner.

HeLa cells as host cells for transfecting the G protein-coupled receptor protein expression plasmid and the reporter plasmid were plated on a 384-well assay plate (COSTAR 3704) at 4000 cells/well in a culture volume of 25 µl, followed by incubation overnight. The medium used was DMEM (Invitrogen) supplemented with 10% fetal calf serum and 1% MEM non-essential amino acids solution (DMEM/NEAA).

Each plasmid was added to and mixed with 240 µl of Opti-MEM-I (Invitrogen) in a proportion of 1 µl of the protein expression plasmid or, for comparison, expression vector pAKKO-111H without DNA encoding the receptor protein in place of an expression plasmid of the receptor, 9 µl of the reporter plasmid and 1 µl each of the G protein-coupled receptor protein expression plasmid Gα0A, Gβ1 or Gγ2. The mixture was mixed with 240 µl of Opti-MEM-I added with 10 µl of Lipofectamine™ 2000 Reagent (Invitrogen) in equal volumes to form the liposome and plasmid complex, in accordance with the procedures in the instruction manuals attached. These mixtures were added to the culture solution of HeLa cells in 5 µl each/well to transfect the plasmid, followed by incubation overnight at 37° C. in 5% $CO_2$.

Example 2

Detection of Ligand Activity by Reporter Assay

The HeLa cells prepared in EXAMPLE 1 were washed twice with fetal calf serum-free DMEM/NEAA (assay medium) and then cultured in the same assay medium at 37° C. under 5% $CO_2$ for 2 hours. After the cells were further washed once with the same assay buffer, a solution of sodium taurolithocholate (TLCA) (Sigma) in 0.05% CHAPS-containing assay medium was exposed to the cells in each well. After the sample was added, incubation was conducted at 37° C. under 5% $CO_2$ for 4 hours to induce promotion of the transcription/translation of the reporter gene derived from intracellular signal transduction caused by the agonist activity of a ligand mediated by the receptor. After the incubation was completed, the assay buffer in each well was removed and 8 µl each of PicaGene LT 2.0 (Toyo Ink Mfg. Co., Ltd.) as a substrate for assaying the luciferase activity was added to the well. After the cells were lysed and thoroughly mixed with the substrate, the chemiluminescence level corresponding to the expression induction level of the reporter gene in each well was measured on the plate reader (EnVision™, Perkin-Elmer).

As a result, an increased luciferase activity was noted in the GPR39-expressed cells by the addition of TLCA (5 µM or 20 µM), as shown in TABLE 1. On the other hand, any marked increase of the activity was not detected in the pAKKO-111H transfected cells for control, even when TLCA was added.

TABLE 1

| Increased Luciferase Activity (cps) by TLCA in GPR39-Expressed Cells | | |
|---|---|---|
| TLCA Level (µM) | GPR39 | pAKKO-111H (control) |
| 0 | 3574 | 2042 |
| 5 | 5977 | 2214 |
| 20 | 8114 | 2542 |

Example 3

Detection of Agonist Activity of Bile Acids on Rat GPR39

Using the CHO cell line where rat GPR39 was stably expressed, the agonist activity of bile acids was assayed by FLIPR (Molecular Devices) in terms of an intracellular calcium increasing activity as an indicator. The CHO cell line used where rat GPR39 was stably expressed was cultured in HAM's αMEM (Invitrogen) supplemented with 10% fetal calf serum. On the day before the assay, human GPR39-expressed cell line was cultured in a culture flask until confluent, washed with PBS, detached using trypsin, centrifuged for recovery and then suspended in a medium to $3 \times 10^5$ cells/ml. After a 100 µl aliquot was dispensed into each well of a black walled 96-well plate (Costar), followed by incubation overnight in a $CO_2$ incubator.

On the assay day, various test samples were added to the cells prepared on the preceding day, and on that occasion, changes in intracellular calcium level were assayed on FLIPR. To assay for changes in intracellular calcium level on FLIPR, the following pretreatment was performed. First, an assay buffer was prepared to add fluorescence dye Fluo-3AM (DOJIN) to the cells or wash the cells immediately before the FLIPR assay. First, an assay buffer was prepared for use to add fluorescence dye Fluo-3AM (DOJIN) to cells or wash the cells immediately before the FLIPR assay. To 1000 ml of HBSS (Invitrogen) supplemented with 20 ml of IM HEPES (pH7.4) (DOJIN) (hereinafter HBSS/HEPES solution), 10 ml of a solution prepared by dissolving 710 mg of Probenecid (Sigma) in 5 ml of IN NaOH and further adding 5 ml of the HBSS/HEPES solution thereto was added, and the resulting solution was used as the assay buffer. Next, 50 µg of Fluo-3AM (DOJIN) was dissolved in 21 µl of DMSO (DOJIN) and an equal volume of 20% Pluronic acid (Molecular Probes) was further added to and mixed with the solution. The mixture was then added to 10.6 ml of the assay buffer supplemented with 105 µl of fetal calf serum to prepare a fluorescence dye solution. The medium of the CHO cells which stably expressed rat GPR39 was removed. Immediately thereafter, the fluorescence dye solution was dispensed in 100 µl each/well and the cells were incubated at 37° C. in a $CO_2$ incubator for an hour so that the fluorescence dye was taken up into the cells. The cells after the incubation were washed with the assay buffer described above. Test samples added to the cells which stably expressed rat GPR39 were prepared using the assay buffer and set on FLIPR at the same time. Following the pretreatment above, changes in intracellular calcium level after addition of various test samples were determined. As shown in FIG. 1 wherein the intracellular calcium increasing activity is given on the ordinate as a count in terms of changes in fluorescence intensity and time is given by second on the abscissa, when 50 or 10 µM bile acid (taurolithocholic acid) was added, the intracellular calcium level of CHO/rGPR39 was dose-dependently increased and the agonist activity on rat GPR39 was detected.

Example 4

Analysis of Tissue Distribution of GPR39mRNA in Rat by RT-PCR

Various organs were removed from Wistar rats and total RNA was prepared using Isogen (Nippon Gene) in accordance with the manual. Following the manual, cDNA was synthesized from 1µ of the obtained total RNA using random primer and SuperScriptII reverse transcriptase (GIBCO BRL). The cDNA synthesized was rendered a solution of 25 ng/µl when calculated as the total RNA and used as a template for the subsequent RT-PCR. For RT-PCR, Sequence Detection System Prism 7900 (PE Biosystems) was used; as primers for amplification and detection, 5'-CCCATGGAGTTC-TACAGCATCAT-3' (SEQ ID NO: 7) and 5'-TGTGGAGCTTGCAGGACAGA-3' (SEQ ID NO: 8) were used and 5'-(Fam)-TGGAACCCCCTGACCACAC-CCA-(Tamra)-3' (SEQ ID NO: 9) was used as TaqMan probe. For the RT-PCR solution, 0.135 µl each of the 100 µM primer solutions, 0.75 µl of 5 µM TaqMan probe and 1 µl of the cDNA solution prepared above were added to 7.5 µl of TaqMan Universal PCR Master Mix (PE Biosystems, Inc.), and distilled water was added thereto to make the total volume of the reaction solution 15 µl. PCR was carried out by reacting at 50° C. for 2 minutes and 95° C. for 10 minutes, then repeating 40 times the cycle set to include 95° C. for 15 seconds and 60° C. for 1 minute. The expression level of mRNA for the GPR39 obtained in various rat tissues were calculated in terms of the number of copies per total RNA 25 ng (FIG. 2).

Example 5

Secretion Promotion of IL-8 from GPR39-Expressed UM-UC-3 by Bile Acids

Using the GPR39-expressed cell line UM-UC-3 (Dainippon Pharmaceutical), effects by the addition of bile acids as the GPR39 agonist were examined.

On the day before assay, UM-UC-3 was cultured until preconfluent in MINIMUM ESSENTIAL MEDIUM (WITH EARLE'S SALTS, WITH L-GLUTAMINE) (GIBCO BRL) supplemented with 10% FCS and MEM NON-ESSENTIAL AMINO ACIDS (GIBCO BRL), washed with PBS, detached using trypsin, centrifuged for recovery and then suspended in a medium to $3 \times 10^6$ cells/ml. After a 100 µl aliquot was dispensed into each well of a 96-well plate (Falcon), followed by incubation overnight in a $CO_2$ incubator.

On the assay day, after the medium for the cells prepared on the preceding day was removed, the cells were washed with MEM NON-ESSENTIAL AMINO ACIDS-containing MINIMUM ESSENTIAL MEDIUM (WITH EARLE'S SALTS, WITH L-GLUTAMINE). A 5 ml aliquot was further charged in each well, followed by incubation overnight for an hour at 37° C. in a $CO_2$ incubator. Subsequently, a 100 µl aliquot of MEM NON-ESSENTIAL AMINO ACIDS-containing MINIMUM ESSENTIAL MEDIUM (WITH EARLE'S SALTS, WITH L-GLUTAMINE), to which various test samples were added, was dispensed into each well, followed by incubation overnight at 37° C. in a $CO_2$ incubator for 4 hours. After the culture supernatant was recovered, IL-8 contained in each sample was quantified by EIA (Amersham). As a result, it was confirmed that IL-8 accumulated approximately twice as much in the presence of 500 µM taurine conjugate of deoxycholic acid, when compared to in the absence of the conjugate. This reveals that the GPR39 promotes the secretion of cytokines such as IL-8 or the like as one of its functions.

INDUSTRIAL APPLICABILITY

By using the GPR39 and the cholesterol metabolism-related protein as its ligand, compounds that alter the binding property of the cholesterol metabolism-related protein to the GPR39 can be efficiently screened. In addition, agonists having more potent activities can be found using the screening method of the present invention.

The antagonists for the GPR39 are useful as agents for preventing/treating (i) inflammatory bowel disorders [e.g., (a) ulcerative colitis as gastrointestinal disturbances associated with regulation of nerve cells in the organ, Crohn's disease, irritable bowel syndrome; (b) infections with bacteria, fungi, viruses, protozoa, etc.; (c) infectious colitis caused by constriction of blood flow, exposure to radiation, administration of antibiotics, etc. (e.g., intestinal tuberculosis, amebic dysentery, pseudomenbranous colitis (*campylobacter* enteritis, *salmonella* enteritis, *Yersinia* enteritis, *Vibrio parahaemolyticus* enteritis, bacillary dysentery), schistosomiasis, fungal or viral colitis, drug hemorrhagic colitis, ischemic colitis, obstructive colitis, solitary rectal ulcer, radiation enterocolitis, simple ulcer)], (ii) functional bowel disorders caused by gastrointestinal motility disturbances, (iii) irritable bowel syndrome, (iv) fecal incontinence, (v) colitis or (vi) posttransplantational hyperimmunization, etc., or as antiemetic agents for vomiting which might be induced by functional bowel disorders caused by gastrointestinal motility disturbances, irritable bowel syndrome, fecal incontinence, colitis or Crohn's disease; or the like.

The agonists for the GPR39 (preferably the agonist that potentiates the signal transduction induced by binding of the cholesterol metabolism-related protein to the GPR39) are useful as agents for preventing/treating, for example, growth retardation, lacerations, burn injury, poor circulation, decline in learning ability, hypogonadism, dysgeusia, anosmia, hyperplasia, arteriosclerosis, myocardial infarction, apoplexy, hepatic cirrhosis, cholesterol accumulation, reduced resistance to infections, gout, cancer, hard labor, mellitus diabetes, blemish, anemia, depilation, respiratory disorders, indigestion, cardiopathy, gray hair, swelling, wrinkle, skin sagging, hypothyroidism, depression, irregular periods, hypotonic bladder based on sensory decrease of the bladder or hypotonic bladder accompanied by sensory paralysis of the bladder after surgery of the pelvic viscera, or constipation (preferably constipation), or the like.

The invention claimed is:

1. A method of screening (I) a compound or its salt that alters the binding property of a G protein-coupled receptor protein or a salt thereof, to a bile acid, or (II) a compound or its salt that modulates signal transduction induced by binding of said receptor protein or a salt thereof to a bile acid, wherein said method comprises:
   a) contacting a bile acid with the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof, and measuring (i) the amount of said bile acid bound to said G protein-coupled receptor protein or said protein or salts thereof, or (ii) signal transduction mediated by said G protein-coupled receptor protein or said protein or salts thereof; and
   b) contacting a bile acid and a test compound with the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof, and measuring (i) the amount of said bile acid bound to said G protein-coupled receptor protein or said protein or salts thereof, or (ii) signal transduction mediated by said G protein-coupled receptor protein or said protein or salts thereof; and
   c) comparing binding property or signal transduction between a) and b).

2. A method of screening an agonist for or antagonist to a G protein-coupled receptor protein or a salt thereof, wherein said method comprises:
   a) contacting a bile acid with the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof, and measuring the amount of said bile acid bound to said G protein-coupled receptor protein or said protein or salts thereof; and
   b) contacting a bile acid and a test compound with the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof, and measuring the amount of said bile acid bound to said G protein-coupled receptor protein or said protein or salts thereof; and
   c) comparing binding property between a) and b);
wherein a decrease in binding measured in step b) compared to step a) indicates the test compound is an agonist or an antagonist.

3. The screening method according to claim 1, wherein the G protein-coupled receptor protein is a G protein-coupled receptor protein consisting of the amino acid sequence of SEQ ID NO: 1, SEQ ID NO: 3 or SEQ ID NO: 5.

4. A kit for screening (I) a compound or its salt that alters the binding property of a G protein-coupled receptor protein or a salt thereof, to a bile acid, or (II) a compound or its salt that modulates signal transduction induced by binding of said receptor protein or a salt thereof to a bile acid, which comprises (1) the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof, and (2) the bile acid.

5. A kit for screening an agonist for or antagonist to a G protein-coupled receptor protein or a salt thereof, which comprises (1) the G protein-coupled receptor protein containing the amino acid sequence of SEQ ID NO: 1 or a protein containing an amino acid sequence having at least 80% homology to the amino acid sequence of SEQ ID NO: 1 and having the same ligand binding activity as the receptor consisting of the amino acid sequence of SEQ ID NO: 1 or the salts thereof and (2) a compound or its salt that alters the binding property of said receptor protein or a salt thereof to a bile acid.

* * * * *